(12) United States Patent
Magee et al.

(10) Patent No.: US 10,555,758 B2
(45) Date of Patent: Feb. 11, 2020

(54) TAPPING DEVICES, SYSTEMS AND METHODS FOR USE IN BONE TISSUE

(71) Applicant: Woven Orthopedic Technologies, LLC, Manchester, CT (US)

(72) Inventors: Francis Patrick Magee, Mackay, ID (US); Robert Luzzi, Silverthorne, CO (US); Jeffrey P. Radziunas, Wallingford, CT (US); Lynn MacDonald, Bantam, CT (US)

(73) Assignee: Woven Orthopedic Technologies, LLC, Manchester, CT (US)

( * ) Notice: Subject to any disclaimer, the term of this patent is extended or adjusted under 35 U.S.C. 154(b) by 220 days.

(21) Appl. No.: 15/230,198

(22) Filed: Aug. 5, 2016

(65) Prior Publication Data
US 2017/0035482 A1   Feb. 9, 2017

Related U.S. Application Data

(60) Provisional application No. 62/201,273, filed on Aug. 5, 2015, provisional application No. 62/287,756, filed on Jan. 27, 2016.

(51) Int. Cl.
| | |
|---|---|
| *A61B 17/86* | (2006.01) |
| *A61B 17/68* | (2006.01) |
| *A61B 17/88* | (2006.01) |
| *A61L 31/02* | (2006.01) |

(52) U.S. Cl.
CPC .......... *A61B 17/686* (2013.01); *A61B 17/863* (2013.01); *A61B 17/8872* (2013.01); *A61L 31/028* (2013.01); *A61B 2017/8655* (2013.01); *A61L 2430/02* (2013.01)

(58) Field of Classification Search
CPC ...... A61B 17/86; A61B 17/863; A61B 17/869
See application file for complete search history.

(56) References Cited

U.S. PATENT DOCUMENTS

| | | |
|---|---|---|
| 517,668 A | 4/1894 | Still |
| 1,486,527 A | 3/1924 | Larkin |
| 1,516,652 A | 11/1924 | Tomkinson |

(Continued)

FOREIGN PATENT DOCUMENTS

| | | |
|---|---|---|
| CN | 201046258 Y | 4/2008 |
| CN | 201073336 Y | 6/2008 |

(Continued)

OTHER PUBLICATIONS

NuVasive, Inc.; Patent Issued for Orthopedic Screw Insert, dated Feb. 23, 2015.

(Continued)

*Primary Examiner* — Christopher J Beccia
(74) *Attorney, Agent, or Firm* — Venable LLP; Michele V. Frank

(57) ABSTRACT

A soft tapping device for preparing a bone hole that includes a substantially cylindrical insert that is sized to enter into a compressed woven retention device. The substantially cylindrical insert has protrusions that are adaptable to expand portions of a compressed woven retention device inside the bone hole. The substantially cylindrical insert is also configured to exit from the compressed woven retention device without changing the expanded portions of the compressed woven retention device.

26 Claims, 13 Drawing Sheets

(56) References Cited

U.S. PATENT DOCUMENTS

| | | |
|---|---|---|
| 1,517,668 A | 12/1924 | Daudelin |
| 2,148,164 A | 2/1939 | Krippendorf |
| 2,326,453 A | 8/1943 | Gelpcke |
| 2,388,693 A | 11/1945 | Jeckel |
| 2,879,687 A | 3/1959 | Leimbach |
| 2,936,670 A | 5/1960 | Walter |
| 2,983,182 A | 5/1961 | Shobert |
| 3,054,406 A | 9/1962 | Usher |
| 3,187,752 A | 6/1965 | Glick |
| 3,199,398 A | 8/1965 | Weisz |
| 3,232,163 A | 2/1966 | Croessant |
| 3,363,502 A | 1/1968 | Florentine |
| 3,371,573 A | 3/1968 | Koreki |
| 3,710,789 A | 1/1973 | Ersek |
| 3,714,862 A | 2/1973 | Berger |
| 3,921,496 A | 11/1975 | Helderman |
| 4,011,602 A | 3/1977 | Rybicki et al. |
| 4,064,567 A | 12/1977 | Burstein et al. |
| 4,158,984 A | 6/1979 | Griffiths |
| 4,182,339 A | 1/1980 | Hardy, Jr. |
| 4,205,399 A | 6/1980 | Shalaby et al. |
| 4,304,169 A | 12/1981 | Cimprich et al. |
| 4,383,527 A | 5/1983 | Asnis et al. |
| 4,394,370 A | 7/1983 | Jefferies |
| 4,409,974 A | 10/1983 | Freedland |
| 4,453,539 A | 6/1984 | Raftopoulos et al. |
| 4,520,821 A | 6/1985 | Schmidt et al. |
| 4,563,489 A | 1/1986 | Urist |
| 4,566,466 A | 1/1986 | Ripple et al. |
| 4,567,917 A | 2/1986 | Millard |
| 4,584,722 A | 4/1986 | Levy et al. |
| 4,610,688 A | 9/1986 | Silvestrini et al. |
| 4,640,271 A | 2/1987 | Lower |
| 4,693,721 A | 9/1987 | Ducheyne |
| 4,708,132 A | 11/1987 | Silvestrini |
| 4,711,232 A | 12/1987 | Fischer et al. |
| 4,716,807 A | 1/1988 | Fischer |
| 4,716,893 A | 1/1988 | Fischer et al. |
| 4,753,149 A | 6/1988 | Celani |
| 4,760,843 A | 8/1988 | Fischer et al. |
| 4,776,330 A | 10/1988 | Chapman et al. |
| 4,777,860 A | 10/1988 | Bassett et al. |
| 4,790,852 A | 12/1988 | Noiles |
| 4,803,909 A | 2/1989 | Smith |
| 4,870,957 A | 10/1989 | Goble et al. |
| 4,894,063 A | 1/1990 | Nashef |
| 4,913,028 A | 4/1990 | Yoshiya |
| 4,917,700 A | 4/1990 | Aikins |
| 5,013,318 A | 5/1991 | Spranza, III |
| 5,041,114 A | 8/1991 | Chapman et al. |
| 5,059,211 A | 10/1991 | Stack et al. |
| 5,084,050 A | 1/1992 | Draenert |
| 5,171,148 A | 12/1992 | Wasserman et al. |
| 5,186,992 A | 2/1993 | Kite, III |
| 5,211,647 A | 5/1993 | Schmieding |
| 5,221,261 A | 6/1993 | Termin et al. |
| 5,257,571 A | 11/1993 | Richardson |
| 5,268,001 A | 12/1993 | Nicholson et al. |
| 5,300,075 A | 4/1994 | Gordon |
| 5,354,292 A | 10/1994 | Braeuer et al. |
| 5,380,334 A | 1/1995 | Torrie et al. |
| 5,383,387 A | 1/1995 | Chesterfield et al. |
| 5,385,077 A | 1/1995 | Akiyama et al. |
| 5,443,499 A | 8/1995 | Schmitt |
| 5,456,721 A | 10/1995 | Legrand |
| 5,458,601 A | 10/1995 | Young, Jr. et al. |
| 5,490,750 A | 2/1996 | Gundy |
| 5,501,133 A | 3/1996 | Brookstein et al. |
| 5,520,084 A | 5/1996 | Chesterfield et al. |
| 5,571,184 A | 11/1996 | DeSatnick |
| 5,628,788 A | 5/1997 | Pinchuk |
| 5,629,077 A | 5/1997 | Turnlund et al. |
| 5,641,256 A | 6/1997 | Gundy |
| 5,713,904 A | 2/1998 | Errico et al. |
| 5,716,359 A | 2/1998 | Ojima et al. |
| 5,718,159 A | 2/1998 | Thompson |
| 5,725,541 A | 3/1998 | Anspach, III et al. |
| 5,741,325 A | 4/1998 | Chaikof et al. |
| 5,756,457 A | 5/1998 | Wang et al. |
| 5,758,562 A | 6/1998 | Thompson |
| 5,766,250 A | 6/1998 | Chervitz et al. |
| 5,785,713 A | 7/1998 | Jobe |
| D397,794 S | 9/1998 | Geber |
| 5,849,013 A | 12/1998 | Whittaker et al. |
| 5,871,504 A | 2/1999 | Eaton et al. |
| 5,876,432 A | 3/1999 | Lau et al. |
| 5,904,685 A | 5/1999 | Walawalkar |
| 5,935,129 A | 8/1999 | McDevitt et al. |
| 5,941,901 A | 8/1999 | Egan |
| 5,957,974 A | 9/1999 | Thompson et al. |
| 5,961,524 A | 10/1999 | Crombie |
| 5,981,926 A | 11/1999 | Kim |
| 5,984,926 A | 11/1999 | Jones |
| 6,019,786 A | 2/2000 | Thompson |
| 6,039,740 A | 3/2000 | Olerud |
| 6,042,592 A | 3/2000 | Schmitt |
| 6,056,751 A | 5/2000 | Fenton, Jr. |
| 6,068,632 A | 5/2000 | Carchidi et al. |
| 6,080,155 A | 6/2000 | Michelson |
| 6,099,530 A | 8/2000 | Simonian et al. |
| 6,126,663 A | 10/2000 | Hair |
| 6,143,029 A * | 11/2000 | Rippstein .................. A61F 2/08 602/36 |
| 6,231,606 B1 | 5/2001 | Graf et al. |
| 6,241,757 B1 | 6/2001 | An et al. |
| 6,264,676 B1 | 7/2001 | Gellman et al. |
| 6,283,966 B1 | 9/2001 | Houfburg |
| 6,314,856 B1 | 11/2001 | Keith et al. |
| 6,319,255 B1 | 11/2001 | Grundei et al. |
| 6,325,822 B1 | 12/2001 | Chouinard et al. |
| 6,336,940 B1 | 1/2002 | Graf et al. |
| 6,342,068 B1 | 1/2002 | Thompson |
| 6,355,044 B1 | 3/2002 | Hair |
| 6,375,662 B1 | 4/2002 | Schmitt |
| 6,398,807 B1 | 6/2002 | Chouinard et al. |
| 6,413,260 B1 | 7/2002 | Berrevoets et al. |
| 6,436,142 B1 | 8/2002 | Paes et al. |
| 6,450,770 B1 | 9/2002 | Wang et al. |
| 6,495,227 B1 | 12/2002 | Cahuzac |
| 6,500,203 B1 | 12/2002 | Thompson et al. |
| 6,540,770 B1 | 4/2003 | Tornier et al. |
| 6,544,281 B2 | 4/2003 | ElAttrache et al. |
| 6,551,352 B2 | 4/2003 | Clerc et al. |
| 6,562,046 B2 | 5/2003 | Sasso |
| 6,582,461 B1 | 6/2003 | Burmeister et al. |
| 6,616,694 B1 | 9/2003 | Hart |
| 6,616,996 B1 | 9/2003 | Keith et al. |
| 6,622,604 B1 | 9/2003 | Chouinard et al. |
| 6,631,666 B2 | 10/2003 | Cahuzac |
| 6,645,211 B2 | 11/2003 | Magana |
| 6,652,571 B1 | 11/2003 | White et al. |
| 6,669,706 B2 | 12/2003 | Schmitt et al. |
| 6,685,738 B2 | 2/2004 | Chouinard et al. |
| 6,746,483 B1 * | 6/2004 | Bojarski ............ A61B 17/0401 623/13.14 |
| 6,767,350 B1 | 7/2004 | Lob |
| 6,792,979 B2 | 9/2004 | Konya et al. |
| 6,814,734 B2 | 11/2004 | Chappuis et al. |
| 6,817,076 B1 | 11/2004 | Stephenson |
| 6,827,743 B2 | 12/2004 | Eisermann et al. |
| 6,840,769 B2 | 1/2005 | Augthun et al. |
| 6,863,692 B2 | 3/2005 | Meulink |
| D503,802 S | 4/2005 | Bjarnason |
| 6,875,216 B2 | 4/2005 | Wolf |
| 6,908,466 B1 | 6/2005 | Bonutti et al. |
| 6,942,666 B2 | 9/2005 | Overaker et al. |
| 6,942,693 B2 | 9/2005 | Chouinard et al. |
| 6,991,647 B2 | 1/2006 | Jadhav |
| 7,004,967 B2 | 2/2006 | Chouinard et al. |
| 7,022,124 B2 | 4/2006 | Takei et al. |
| 7,052,513 B2 | 5/2006 | Thompson |
| 7,093,527 B2 | 8/2006 | Rapaport et al. |
| 7,101,183 B2 | 9/2006 | Augthun et al. |
| 7,141,074 B2 | 11/2006 | Fanger et al. |

(56) References Cited

U.S. PATENT DOCUMENTS

| | | |
|---|---|---|
| 7,144,413 B2 | 12/2006 | Wilford et al. |
| 7,213,495 B2 | 5/2007 | McCullagh et al. |
| 7,237,466 B2 | 7/2007 | Chen |
| 7,255,712 B1 | 8/2007 | Steinberg |
| 7,275,471 B2 | 10/2007 | Nishri et al. |
| 7,279,008 B2 | 10/2007 | Brown et al. |
| 7,309,355 B2 | 12/2007 | Donnelly et al. |
| 7,311,031 B2 | 12/2007 | McCullagh et al. |
| 7,341,592 B1 | 3/2008 | Walters et al. |
| 7,341,601 B2 | 3/2008 | Eisermann et al. |
| 7,344,559 B2 | 3/2008 | Gray et al. |
| 7,407,512 B2 | 8/2008 | Bojarski et al. |
| 7,435,254 B2 | 10/2008 | Chouinard et al. |
| 7,513,865 B2 | 4/2009 | Boume et al. |
| 7,547,321 B2 | 6/2009 | Silvestri et al. |
| 7,569,058 B2 | 8/2009 | Zwimmann |
| 7,572,283 B1 | 8/2009 | Meridew |
| 7,572,298 B2 | 8/2009 | Roller et al. |
| 7,582,108 B2 | 9/2009 | Hierlemann et al. |
| 7,637,949 B2 | 12/2009 | Hart |
| D612,499 S | 3/2010 | Ondracek et al. |
| 7,682,392 B2 | 3/2010 | Serhan et al. |
| 7,699,893 B2 | 4/2010 | Donnelly et al. |
| 7,731,750 B2 | 6/2010 | Bojarski et al. |
| 7,740,657 B2 | 6/2010 | Brown, Jr. et al. |
| 7,749,233 B2 | 7/2010 | Farr et al. |
| 7,758,642 B2 | 7/2010 | Bojarski et al. |
| 7,785,357 B2 | 8/2010 | Guan et al. |
| D626,648 S | 11/2010 | Ahlgren |
| 7,824,433 B2 | 11/2010 | Williams |
| 7,833,249 B2 | 11/2010 | Shaolian et al. |
| 7,846,162 B2 | 12/2010 | Nelson et al. |
| 7,892,203 B2 | 2/2011 | Lenker et al. |
| 7,896,901 B2 | 3/2011 | Whittaker |
| 7,938,853 B2 | 5/2011 | Chouinard et al. |
| 7,963,972 B2 | 6/2011 | Foerster et al. |
| 7,967,851 B2 | 6/2011 | Bickley et al. |
| 7,988,732 B2 | 8/2011 | Bojarski et al. |
| 8,052,720 B2 | 11/2011 | Kuester et al. |
| 8,100,969 B2 | 1/2012 | Hart |
| 8,114,079 B2 | 2/2012 | Haidukewych et al. |
| 8,114,141 B2 | 2/2012 | Appenzeller et al. |
| 8,128,626 B2 | 3/2012 | Justin |
| 8,142,415 B2 | 3/2012 | Warnock, Jr. et al. |
| 8,151,682 B2 | 4/2012 | Lilburn et al. |
| 8,162,998 B2 | 4/2012 | Schlienger et al. |
| 8,163,031 B2 | 4/2012 | Truckai et al. |
| 8,202,306 B2 | 6/2012 | Dreyfuss |
| 8,221,479 B2 | 7/2012 | Glazer et al. |
| 8,226,714 B2 | 7/2012 | Beck, Jr. et al. |
| 8,226,715 B2 | 7/2012 | Hwang et al. |
| 8,241,340 B2 | 8/2012 | Froehlich |
| 8,257,395 B2 | 9/2012 | Bhatnagar et al. |
| 8,298,262 B2 | 10/2012 | Stone et al. |
| 8,308,779 B2 | 11/2012 | Reiley |
| 8,317,799 B2 | 11/2012 | Schon et al. |
| 8,317,863 B2 | 11/2012 | Cauldwell et al. |
| 8,347,772 B2 | 1/2013 | Dow et al. |
| 8,353,941 B2 | 1/2013 | Fricker et al. |
| 8,361,078 B2 | 1/2013 | Beyar et al. |
| 8,366,711 B2 | 2/2013 | Rabiner et al. |
| 8,372,115 B2 | 2/2013 | Kohm et al. |
| 8,382,849 B2 | 2/2013 | Thomas |
| 8,414,635 B2 | 4/2013 | Hyodoh et al. |
| 8,419,780 B2 | 4/2013 | Bickley et al. |
| 8,420,113 B2 | 4/2013 | Zhao |
| 8,435,293 B2 | 5/2013 | Donnelly et al. |
| 8,443,706 B2 | 5/2013 | Egres, Jr. |
| 8,459,164 B2 | 6/2013 | Lilburn et al. |
| 8,493,705 B2 | 7/2013 | Lin et al. |
| 8,496,705 B2 | 7/2013 | Hart |
| 8,506,605 B2 | 8/2013 | Bickley et al. |
| 8,523,902 B2 | 9/2013 | Heaven et al. |
| 8,523,916 B2 | 9/2013 | Anderson et al. |
| 8,523,951 B2 | 9/2013 | Kania |
| 8,545,499 B2 | 10/2013 | Lozier et al. |
| 8,546,456 B2 | 10/2013 | Rose et al. |
| 8,546,546 B2 | 10/2013 | Nakano |
| 8,546,752 B2 | 10/2013 | Henion et al. |
| 8,568,413 B2 | 10/2013 | Mazur et al. |
| 8,585,762 B2 | 11/2013 | Hall |
| 8,591,582 B2 | 11/2013 | Anderson et al. |
| 8,617,185 B2 | 12/2013 | Bonutti et al. |
| 8,628,464 B2 | 1/2014 | Bourne et al. |
| 8,636,753 B2 | 1/2014 | Buevich et al. |
| 8,652,171 B2 | 2/2014 | Stone et al. |
| 8,663,296 B2 | 3/2014 | Williams |
| 8,663,672 B2 | 3/2014 | Manrique et al. |
| 8,671,815 B2 | 3/2014 | Hancock et al. |
| 8,677,874 B2 | 3/2014 | Lilburn et al. |
| 8,690,962 B2 | 4/2014 | Dignam et al. |
| 8,696,748 B2 | 4/2014 | Bojarski et al. |
| 8,709,055 B2 | 4/2014 | Beyar et al. |
| 8,721,519 B2 | 5/2014 | Sheu et al. |
| 8,747,469 B2 | 6/2014 | Wang et al. |
| 8,747,470 B2 | 6/2014 | Beck, Jr. et al. |
| 8,753,391 B2 | 6/2014 | Lu et al. |
| 8,770,081 B2 | 7/2014 | David et al. |
| 8,794,118 B2 | 8/2014 | Dow et al. |
| 8,821,090 B2 | 9/2014 | Gruber |
| 8,833,224 B2 | 9/2014 | Thompson et al. |
| 8,840,677 B2 | 9/2014 | Kale et al. |
| 8,857,304 B2 | 10/2014 | Govari et al. |
| 8,858,606 B2 | 10/2014 | Graf et al. |
| 8,870,877 B2 | 10/2014 | Koogle, Jr. |
| 8,910,554 B2 | 12/2014 | Kinugasa |
| D723,166 S | 2/2015 | Igaki et al. |
| 8,951,293 B2 | 2/2015 | Glazer et al. |
| 8,956,394 B1 | 2/2015 | McDonnell |
| 8,956,410 B2 | 2/2015 | Donnelly et al. |
| 8,992,537 B1 | 3/2015 | McDonnell |
| 9,011,440 B2 | 4/2015 | Schlienger et al. |
| 9,060,809 B2 | 6/2015 | Tipirneni et al. |
| D740,427 S | 10/2015 | McDonnell et al. |
| 9,388,517 B2 | 7/2016 | Lilburn et al. |
| 9,416,472 B2 | 8/2016 | Scherrible et al. |
| 9,532,806 B2 | 1/2017 | McDonnell |
| 9,585,695 B2 | 3/2017 | Jones et al. |
| 9,907,593 B2 | 3/2018 | McDonnell |
| 9,943,351 B2 | 4/2018 | McDonnell et al. |
| 2002/0055749 A1 | 5/2002 | Esnouf et al. |
| 2002/0083821 A1 | 7/2002 | Uchida |
| 2002/0143340 A1 | 10/2002 | Kaneko |
| 2002/0147454 A1 | 10/2002 | Neto |
| 2003/0036761 A1 | 2/2003 | Smothers et al. |
| 2003/0045880 A1 | 3/2003 | Michelson |
| 2004/0024456 A1 | 2/2004 | Brown, Jr. et al. |
| 2004/0068267 A1 | 4/2004 | Harvie et al. |
| 2004/0094024 A1 | 5/2004 | Kim |
| 2004/0133204 A1 | 7/2004 | Davies |
| 2004/0176767 A1 | 9/2004 | Bickley |
| 2005/0015154 A1 | 1/2005 | Lindsey et al. |
| 2005/0070930 A1 | 3/2005 | Kammerer |
| 2005/0150370 A1 | 7/2005 | Nishri et al. |
| 2005/0216006 A1 | 9/2005 | Orbay et al. |
| 2005/0216012 A1 | 9/2005 | Willmen |
| 2005/0251143 A1 | 11/2005 | Dillard |
| 2005/0255230 A1 | 11/2005 | Clerc et al. |
| 2006/0089646 A1 | 4/2006 | Bonutti |
| 2006/0129148 A1 | 6/2006 | Simmons et al. |
| 2007/0038221 A1 | 2/2007 | Fine et al. |
| 2007/0060923 A1 | 3/2007 | Dreyfuss |
| 2007/0093899 A1 | 4/2007 | Dutoit et al. |
| 2007/0118131 A1 | 5/2007 | Gooch |
| 2007/0118144 A1 | 5/2007 | Truckai et al. |
| 2007/0191956 A1 | 8/2007 | Prewett et al. |
| 2007/0250114 A1 | 10/2007 | Drapeau |
| 2007/0270941 A1 | 11/2007 | Headley et al. |
| 2008/0027445 A1 | 1/2008 | Brown et al. |
| 2008/0051793 A1 | 2/2008 | Erickson et al. |
| 2008/0221623 A1 | 9/2008 | Gooch |
| 2008/0221624 A1 | 9/2008 | Gooch |
| 2008/0255560 A1 | 10/2008 | Myers et al. |
| 2008/0262630 A1 | 10/2008 | Fulmer et al. |

(56) References Cited

U.S. PATENT DOCUMENTS

| | | |
|---|---|---|
| 2008/0281430 A1 | 11/2008 | Kelman et al. |
| 2009/0024147 A1 | 1/2009 | Ralph et al. |
| 2009/0136898 A1 | 5/2009 | Kim |
| 2009/0192609 A1 | 7/2009 | Klabunde et al. |
| 2009/0193961 A1 | 8/2009 | Jensen et al. |
| 2009/0216338 A1 | 8/2009 | Gingras et al. |
| 2009/0254124 A1 | 10/2009 | Bickley et al. |
| 2009/0279980 A1* | 11/2009 | Gruber .......... F16B 13/04 411/22 |
| 2009/0306777 A1 | 12/2009 | Widmer et al. |
| 2010/0015286 A1 | 1/2010 | Ghodsian et al. |
| 2010/0016940 A1 | 1/2010 | Shokoohi et al. |
| 2010/0042293 A1 | 2/2010 | Moshchuk et al. |
| 2010/0076503 A1 | 3/2010 | Beyar et al. |
| 2010/0125273 A1 | 5/2010 | Schwieger et al. |
| 2010/0152786 A1 | 6/2010 | Behrbalk |
| 2010/0168505 A1 | 7/2010 | Inman et al. |
| 2010/0179591 A1 | 7/2010 | Saltzman et al. |
| 2010/0185244 A1 | 7/2010 | Gooch |
| 2010/0292738 A1 | 11/2010 | Reiley |
| 2010/0318085 A1 | 12/2010 | Austin et al. |
| 2010/0324607 A1 | 12/2010 | Davis |
| 2010/0331881 A1 | 12/2010 | Hart |
| 2011/0061519 A1 | 3/2011 | Fields |
| 2011/0106177 A1 | 5/2011 | Lewis |
| 2011/0144766 A1 | 6/2011 | Kale et al. |
| 2011/0184472 A1 | 7/2011 | Niederberger et al. |
| 2011/0213467 A1 | 9/2011 | Lozier et al. |
| 2011/0230948 A1 | 9/2011 | Ehrenreich et al. |
| 2011/0238069 A1 | 9/2011 | Zajac et al. |
| 2012/0065649 A1 | 3/2012 | Towler |
| 2012/0123416 A1 | 5/2012 | Gelfand et al. |
| 2012/0172934 A1 | 7/2012 | Fisher et al. |
| 2012/0239145 A1 | 9/2012 | Peterson et al. |
| 2012/0245704 A1 | 9/2012 | Childs |
| 2012/0259372 A1 | 10/2012 | Glazer et al. |
| 2012/0264084 A1 | 10/2012 | Hansson et al. |
| 2013/0013065 A1 | 1/2013 | Bills |
| 2013/0014544 A1 | 1/2013 | Winkler |
| 2013/0018318 A1 | 1/2013 | Ravichandran et al. |
| 2013/0103166 A1 | 4/2013 | Butler et al. |
| 2013/0131684 A1 | 5/2013 | Farrell |
| 2013/0178946 A1 | 7/2013 | Monaghan et al. |
| 2013/0184819 A1 | 7/2013 | Donnelly et al. |
| 2013/0226204 A1 | 8/2013 | Kumar |
| 2013/0289621 A1 | 10/2013 | Fulmer et al. |
| 2014/0046454 A1 | 2/2014 | Rose et al. |
| 2014/0052178 A1 | 2/2014 | Dooney, Jr. |
| 2014/0090549 A1 | 4/2014 | Hurlen |
| 2014/0094805 A1 | 4/2014 | Bonutti et al. |
| 2014/0094860 A1 | 4/2014 | Reimels |
| 2014/0100590 A1 | 4/2014 | Gingras et al. |
| 2014/0128916 A1 | 5/2014 | Williams |
| 2014/0135906 A1 | 5/2014 | Winner et al. |
| 2014/0171946 A1 | 6/2014 | Benson et al. |
| 2014/0194938 A1 | 7/2014 | Bojarski et al. |
| 2014/0207145 A1 | 7/2014 | Sennett |
| 2014/0243978 A1 | 8/2014 | Beck, Jr. et al. |
| 2014/0277150 A1 | 9/2014 | Jones et al. |
| 2014/0277449 A1 | 9/2014 | Jones |
| 2014/0358145 A1 | 12/2014 | Schaller et al. |
| 2015/0018878 A1 | 1/2015 | Rizk et al. |
| 2015/0045831 A1 | 2/2015 | Allen |
| 2015/0119984 A1 | 4/2015 | Donnelly et al. |
| 2015/0148883 A1 | 5/2015 | Hyodoh et al. |
| 2015/0238205 A1 | 8/2015 | Reiley |
| 2015/0275408 A1 | 10/2015 | Tahara et al. |
| 2015/0313720 A1 | 11/2015 | Lorio |
| 2015/0342764 A1 | 12/2015 | Ramzipoor et al. |
| 2016/0010248 A1 | 1/2016 | Lariviere et al. |
| 2016/0038187 A1 | 2/2016 | McDonnell |
| 2016/0038206 A1 | 2/2016 | McDonnell |
| 2016/0058524 A1 | 3/2016 | Tehrani et al. |
| 2016/0074071 A1 | 3/2016 | McDonnell et al. |
| 2016/0074072 A1 | 3/2016 | McDonnell et al. |
| 2016/0074084 A1 | 3/2016 | McDonnell et al. |
| 2016/0168769 A1 | 6/2016 | McDonnell |
| 2016/0183942 A1 | 6/2016 | Allen |
| 2016/0317332 A1 | 11/2016 | Lilburn et al. |
| 2016/0345676 A1 | 12/2016 | Bruce et al. |
| 2017/0035481 A1 | 2/2017 | Magee et al. |
| 2017/0035482 A1 | 2/2017 | Magee et al. |
| 2017/0071634 A1 | 3/2017 | McDonnell |
| 2017/0128100 A1 | 5/2017 | Jones et al. |
| 2017/0165077 A1 | 6/2017 | McDonnell |
| 2017/0215934 A1 | 8/2017 | McDonnell |

FOREIGN PATENT DOCUMENTS

| | | |
|---|---|---|
| EP | 0409364 A2 | 1/1991 |
| EP | 1614402 A1 | 1/2006 |
| FR | 2691626 A1 | 12/1993 |
| FR | 2725615 A1 | 4/1996 |
| FR | 2955259 A1 | 7/2011 |
| GB | 2 307 179 A | 5/1997 |
| JP | 10043199 A | 2/1998 |
| WO | 1983002555 A1 | 8/1983 |
| WO | 1989001320 A1 | 2/1989 |
| WO | 1994007425 A1 | 4/1994 |
| WO | 1996003084 A1 | 2/1996 |
| WO | 2001056506 A1 | 8/2001 |
| WO | 2001070135 A2 | 9/2001 |
| WO | 2006105935 A1 | 10/2006 |
| WO | 2007103404 A2 | 9/2007 |
| WO | 2010042293 A1 | 4/2010 |
| WO | 2012024806 A1 | 3/2012 |
| WO | 2012116319 A2 | 8/2012 |
| WO | 2012121726 A1 | 9/2012 |
| WO | 2013004763 A1 | 1/2013 |
| WO | 2013186525 A1 | 12/2013 |
| WO | 2015097416 A1 | 7/2015 |
| WO | 2016022491 A1 | 2/2016 |
| WO | 2016044471 A1 | 3/2016 |
| WO | 2017024277 A1 | 2/2017 |
| WO | 2017024280 A1 | 2/2017 |

OTHER PUBLICATIONS

Brown et al., "Intratunnel Tibial Fixation of Soft-Tissue Anterior Cruciate Ligament Grafts: Graft Sleeve and Tapered Screw," Clinical Gate, Nov. 14, 2015.

Camlog, "Surgical Procedure with the Camlog Screw-Line Implant," Nov. 17, 2015.

Arthrex, "The Next Generation in Foot and Ankle Repair and Reconstruction Technology," 2011.

Pechon et al., "Salvaging the Pullout Strength of Stripped Screws in Osteoporotic Bone," Geriatr Orthop Surg Rehabil. Jun. 30, 2013; 4(2): 50-52.

ACE Surgical Supply Co., Inc. Titanium Augmentation Micro Mesh—7, http://www.acesurgical.com/bone-grafting/graft-holding-mesh-foils/mic..., Jun. 19, 2014.

Biomesh® Neurological Patches N3L—Spinal dura-mater substitutes—Cousin Biotech, <http://www.cousin-biotech.com/uk/produit.php?idrubrique=16&idspecialite=35&idproduit=81>, Jun. 19, 2014.

Bioretec—ActivaScrew Cannulated—Surgical Technique, <http://www.bioretec.com/products/pro_orthotrauma/activascrew-cannulated/surgical-technique.php>, Jun. 12, 2014.

ConMed, Fixation Implants, <http://www.conmed.com/products/knee-fixation.php>, Jun. 10, 2014.

GORE-TEX® Soft Tissue Patch, <http://www.goremedical.com/stp/>, Jun. 19, 2014.

Medtronic Sofamor Danek, Vertex® Max, Reconstruction System Surgical Technique, © 2005.

The Open Prosthetics Project: suspension, <http://openprosthetics.org/suspension>, Jun. 16, 2014.

Synthes GmbH, Angular Stable Locking System (ASLS). For angular stable locking of intra-medullary nails, Technique Guide, © Oct. 2008.

Synthes GmbH, DLS Dynamic Locking Screw. Combined with LCP Locking Compression Plate, Instructions for Use, © Oct. 2012.

(56) References Cited

OTHER PUBLICATIONS

VICRYL® (polyglactin 910) Woven Mesh—Ethicon, <http://www.ethicon.com/healthcare-professionals/products/tissue-hernia/mesh/vicryl-polyglactin-910-woven-mesh>.
K.P. Chellamani et al., "Medical textiles using Braiding Technology", Journal of Academia and Industrial Research (JAIR), vol. 2, Issue 1, Jun. 2013, pp. 21-26.
Ho Jung Kang et al., An Experimental Intraarticular Implantation of Woven Carbon Fiber Pad into Osteochondral Defect of the Femoral Condyle in Rabbit, Yonsei Medical Journal, vol. 32, No. 2, 1991, pp. 108-116.
D. S. Muckle et al., "Biological Response to Woven Carbon Fibre Pads in the Knee", The Journal of Bone and Joint Surgery, 1989, 7I-B, pp. 60-62.
Takanobu Nishizuka et al., "Intramedullary-fixation Technique for Long Bone Fragility Fractures Using Bioabsorbable Materials", Orthopedic Research Annual Meeting, Mar. 2014.
Maureen Suchenski et al., "Material Properties and Composition of Soft-Tissue Fixation", Arthroscopy: The Journal of Arthroscopic and Related Surgery, vol. 26, No. 6, Jun. 2010, pp. 821-831.
Stephanie C. Von Plocki, et al., "Biodegradable Sleeves for Metal Implants to Prevent Implant-Associated Infection: An Experimental In Vivo Study in Sheep", Veterinary Surgery, vol. 41, Issue 3, Apr. 2012, pp. 410-421.
Andre Weimann, M.D., et al., "Primary Stability of Bone-Patellar Tendon-Bone Graft Fixation With Biodegradable Pins", Arthroscopy: The Journal of Arthroscopic and Related Surgery, vol. 19, No. 10, Dec. 2003, pp. 1097-1102.
Office Action issued in related Design U.S. Appl. No. 29/524,091 dated Jun. 5, 2015. [Available in IFW].
International Search Report and Written Opinion issued in related International Application No. PCT/US2015/050483, dated Dec. 28, 2015.
International Search Report and Written Opinion issued in related International Application No. PCT/US2015/050506, dated Dec. 14, 2015.
International Search Report and Written Opinion issued in related International Application No. PCT/US2015/065028, dated Feb. 12, 2016.
Notice of Allowance issued in Design U.S. Appl. No. 29/524,091 dated Jan. 25, 2016. [Available in IFW].
Aga et al., "Biomechanical comparison of interference screws and combination screw and sheath devices for soft tissue anterior cruciate ligament reconstruction on the tibial side," Feb. 12, 2013.
International Search Report and Written Opinion issued in related International Application No. PCT/US2016/045899 dated Oct. 11, 2016.
Alves et al., "Injectability Evaluation of Tricalcium Phosphate Bone Cement", J Mater Sci Mater Med., vol. 19(5), 2008 (Abstract).
International Search Report and Written Opinion issued in related International Application No. PCT/US2015/043471, dated Nov. 3, 2015.
International Search Report and Written Opinion issued in related International Application No. PCT/US2016/045903, dated Nov. 2, 2016.
Design U.S. Appl. No. 29/524,091, filed Apr. 16, 2015. [Available in IFW].
Non-Final Office Action issued in related U.S. Appl. No. 14/209,514 dated Jul. 27, 2017 [Available in IFW].
Non-Final Office Action issued in related U.S. Appl. No. 14/569,541 dated Feb. 27, 2017 [Available in IFW].
Non-Final Office Action issued in related U.S. Appl. No. 14/487,895 dated Mar. 24, 2017 [Available in IFW].
Non-Final Office Action issued in related U.S. Appl. No. 14/487,951 dated Mar. 22, 2017 [Available in IFW].
Non-Final Office Action issued in related U.S. Appl. No. 15/359,021 dated Feb. 1, 2017 [Available in IFW].
Notice of Allowance issued in related U.S. Appl. No. 15/359,021 dated Sep. 13, 2017 [Available in IFW].
Notice of Allowance issued in related Design U.S. Appl. No. 29/524,091 dated Jan. 25, 2016 [Available in IFW].
International Search Report and Written Opinion issued in related International Application No. PCT/US2017/065450, dated Mar. 6, 2018.
Supplementary European Search Report in corresponding European Application No. 15829032.0, dated Aug. 10, 2018.

* cited by examiner

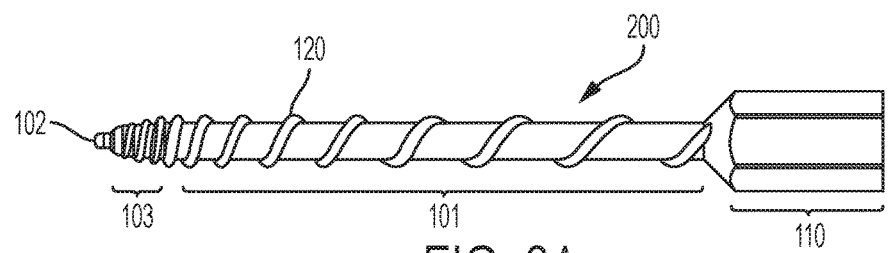
FIG. 3A
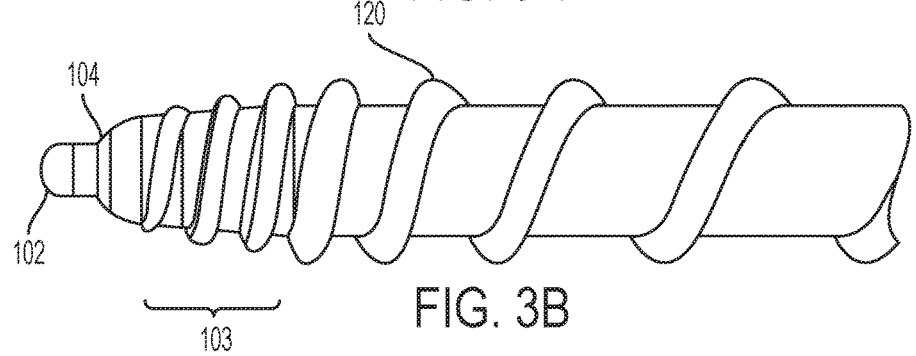
FIG. 3B
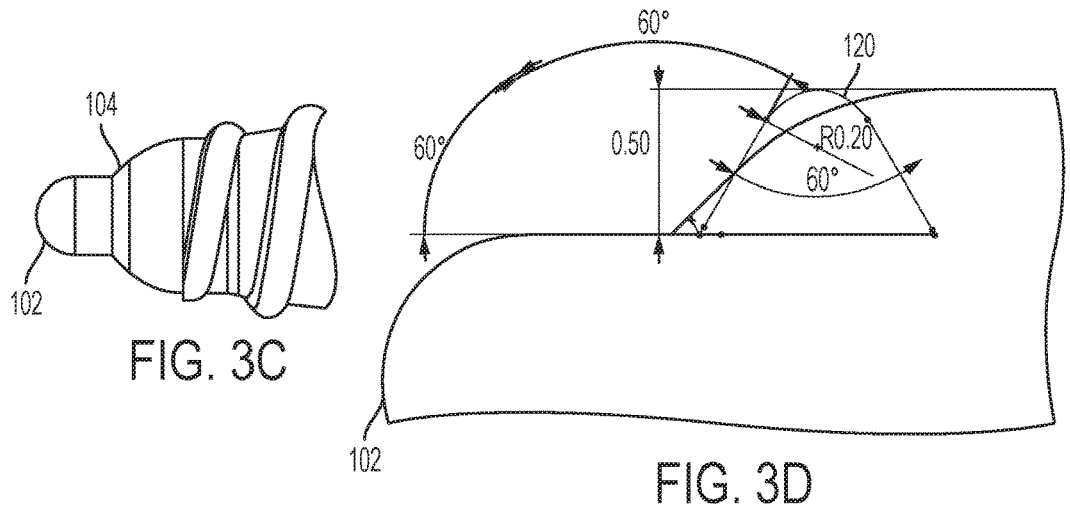
FIG. 3C
FIG. 3D
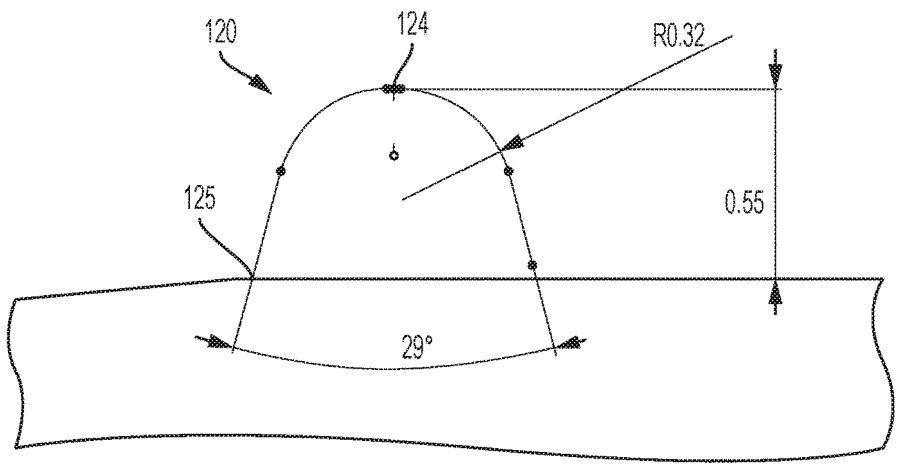
FIG. 3E

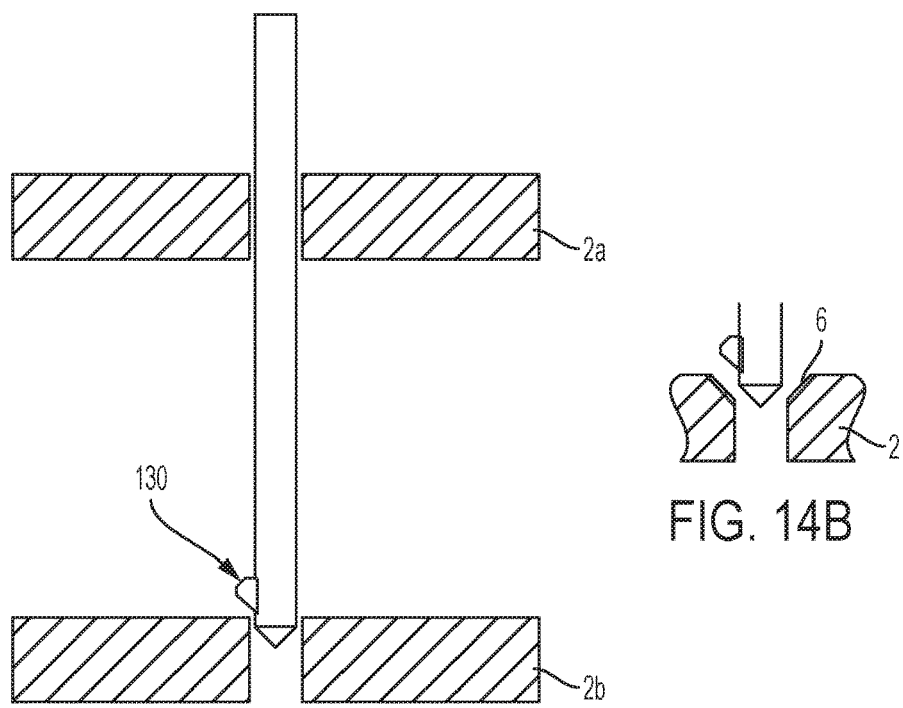
FIG. 14A
FIG. 14B
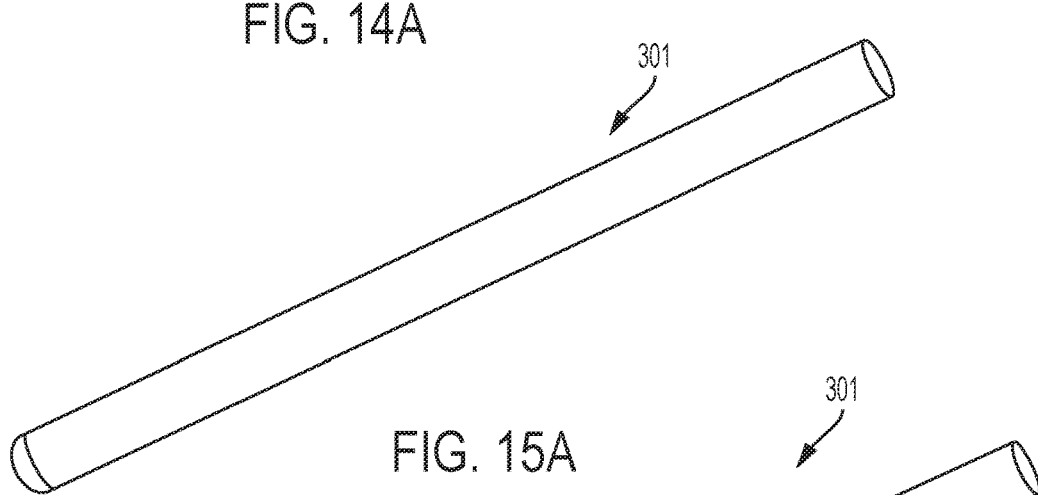
FIG. 15A
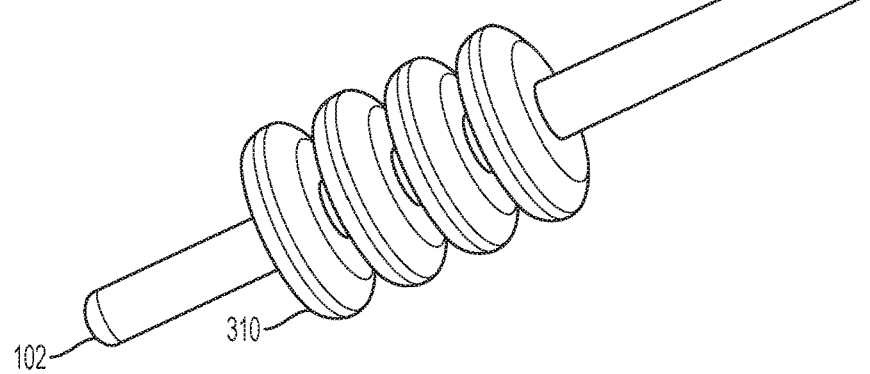
FIG. 15B

TAPPING DEVICES, SYSTEMS AND METHODS FOR USE IN BONE TISSUE

RELATED APPLICATIONS

This application claims priority to U.S. provisional application No. 62/201,273, filed Aug. 5, 2015, and U.S. provisional application No. 62/287,756, filed Jan. 27, 2016.

TECHNICAL FIELD

The present invention relates to devices, systems and methods for use in fixing fasteners to bone tissue.

BACKGROUND

In orthopedic surgery it is common to secure a bone screw to a patient's bone. Bone fracture repair is surgery to fix a broken bone using plates, nails, screws, or pins. It is common in the treatment of fractures to attach a plate to the bone utilizing bone screws. The resulting construct prevents motion of the fractured bone so that the bone can heal. Alternatively, one or more screws may be inserted across the break to hold it in place.

In the treatment of spinal disorders, pedicle screws are inserted into the patient's vertebrae to serve as anchor points that can then be connected with a rod. This construct prevents motion of the vertebral segments that are to be fused.

In the treatment of detached tendons, screw-like tissue anchors are inserted into the patient's bone to serve as an anchor for the reattachment of the tendon.

One complication with the use of bone screws is the loss of fixation or grip between the bone screw and the patient's bone. Another complication with the use of bone screws is the stripping of the hole in the bone when the bone screw is inserted. This results in the loss of purchase and holding strength of the bone screw.

The presence of osteoporotic bone can increase the likelihood of complications by reducing the purchase or grip of the bone screw to the patient's bone, resulting in a loss of holding strength and loosening of the bone screw or pullout of the bone screw.

Current solutions to secure bone screws have not adequately addressed screw failure and the underlying causes of screw failure. Also, current solutions have not adequately addressed screw failure related to bi-cortical intramedullary anchorage.

One solution contemplates utilizing a woven retention device above the bone surface to engage with a bone screw. However, this solution may require precise placement of the woven retention device to prevent interference with screw engagement.

BRIEF SUMMARY OF THE INVENTION

There is a need for devices, systems and methods that enhance the surface of a bone hole to provide enhanced fixation of a bone anchor to the bone. Additionally, there is a need for devices, systems and methods for repairing the surface of the bone hole following damage to the bone hole as in the case of stripping of the hole in the bone when a bone screw is over-tightened. Also, there is a need for devices, systems and methods for providing an enhanced bone hole surface for the reattachment of tendons in, for example anterior/posterior cruciate ligament repair procedures, rotator cuff repair procedures, etc. There is a need for a device that enhances the surface of a bone hole to enhance fixation of a bone anchor to bone and permits bone ingrowth into its structure. There is a need for a single device that enhances the surface of a bone hole to enhance fixation of a bone anchor to bone and accommodates variations in the diameter and depth of the bone hole. Further, there is a need for such devices that have enhanced biocompatibility to aid in tissue and bone healing, regeneration, and growth.

According to an embodiment of the present invention, the level of the material of a woven retention device above the bone surface can be very important. If the level of the woven retention device is too deep then the screw may not find the lumen and/or may push the woven retention device with the screw as the screw proceeds into the lumen. On the other hand, if the woven retention device is too proud, there may be difficulty engaging bone, there may be fiber disruption, or there may be debris formation. Another challenge lies in the general difficulty in engaging bone with the interposition of the woven retention device. For example, a diameter mismatch may occur between the pilot hole and the screw (2.5 mm vs 3.5 mm).

A woven retention device can be reduced in diameter and inserted into a pilot hole that spans a near cortex and a far cortex. In between the near cortex and the far cortex, there is no intramedullary bone in one embodiment. A self-tapping screw can then be inserted into the already inserted woven retention device. The screw upon entering the woven retention device can dilate a portion of the woven retention device back to its natural diameter. As the screw continues to proceed to the end of the woven retention device, the woven retention device continues to dilate to fit. As the screw approaches a far or near cortex or inner cortex bone, an area of a woven retention device that becomes susceptible to breakage or damage as the screw and the bone can pinch or put pressure on a portion of the woven retention device.

To ameliorate this, a soft tapping device is contemplated in accordance with the principles of the invention. The soft tapping device is shown and described herein in various embodiments. The soft tapping device can, any of, contact, engage, compact, compress, expand and/or dilate bone, with respect to the bone inside a bone hole alone, and/or, in combination with a fixation device, for example, a woven retention device.

In one aspect of the invention, a soft tapping device comprises a substantially cylindrical insert sized to enter into a compressed woven retention device, the substantially cylindrical insert having protrusions that are adaptable to expand portions of a compressed woven retention device inside a pilot hole, the substantially cylindrical insert being configured to exit from the compressed woven retention device without changing the expanded portions of the compressed woven retention device. In another aspect of the invention the protrusions are a non-cutting thread having a gradually increasing pitch in a proximal direction along the substantially cylindrical insert. In another aspect of the invention, the protrusions are expanding balloon members that expand in an outward direction when the substantially cylindrical insert is compressed in a longitudinal direction. In another aspect of the invention, the substantially cylindrical insert includes slots which form tensioned slats, wherein the protrusions are the tensioned slats; and the protrusions expand in an outward direction when the substantially cylindrical insert is compressed in a longitudinal direction. In another aspect of the invention, the expanded portions of the compressed portions of the compressed woven retention device allow for a self-tapping screw to insert into the woven retention device without damaging the woven retention device. In another aspect of the invention, the soft tapping device further comprises a shaft with a proximal portion and a distal portion, wherein the distal portion is configured with a non-cutting thread and a rounded end. In another aspect of the invention, the soft tapping device further comprises a shaft with a proximal portion and a distal portion, wherein distal portion is configured with a first thread portion and the proximal portion is configured with a second thread portion with a coarser pitch than first thread portion of the distal portion, and wherein the second thread portion is rounder than the first thread portion.

In another aspect of the invention, a soft tapping device comprises a substantially cylindrical insert configured and sized to expand portions of a substantially cylindrical hole, the substantially cylindrical insert being configured to exit from the hole without changing the expanded portions of the hole. In another aspect of the invention, the soft tapping device further comprises a shaft with a proximal portion and a distal portion, wherein the distal portion is configured with a non-cutting thread. In another aspect of the invention, the non-cutting thread has a radially spiral configuration. In another aspect of the invention, the non-cutting thread has a base and a radially outward-most peak in between the proximal portion and a distal end of the distal portion. In another aspect of the invention, the hole is a bone hole. In another aspect of the invention, the hole is a woven sleeve configured to be disposed in a bone hole. In another aspect of the invention, the hole is a combination of a bone hole and a woven sleeve in the bone hole. In another aspect of the invention, the soft tapping device further comprises a spring-loaded deburring tool on the shaft.

In another aspect of the invention, a method of creating a mantle in a bone comprises inserting a compressed woven retention device into a pilot hole of a bone; inserting a soft tapping device into the compressed woven retention device, wherein the soft tapping device has ridges that, when inserted into the compressed woven retention device, expand the woven retention device with lead in edges; and inserting a self-tapping screw into the expanded woven retention device. In another aspect of the invention, the method further comprises the step of: expanding the inserted woven retention device with a leading edge of a ridge on the soft tapping device. In another aspect of the invention, the method further comprises the step of: removing the soft tapping device without cutting the expanded woven retention device. In another aspect of the invention, the method further comprises the step of: inserting one of a screw and a self-tapping screw into the pilot hole after the soft tapping device is removed. In another aspect of the invention, the method further comprises the step of: inputting a slurry into the pilot hole before inserting the screw.

In another aspect of the invention, a method of creating a mantle for fixation in bone comprises providing a soft tapping device configured to compress material in a bone hole; utilizing a soft tapping device to compress the material in the bone hole; and inserting a woven retention device. In another aspect of the invention, the soft tapping device is configured to provide a surface of the bone hole with soft edges. In another aspect of the invention, the method further comprises inserting a compressed woven retention device into the bone hole, the compressed woven retention device being adapted to expand to fill the soft edges of the bone hole. In another aspect of the invention, the method further comprises inserting a screw into the inserted woven retention device. In another aspect of the invention, inserting the screw comprises inserting a self-tapping screw into the compressed woven retention device. In another aspect of the invention, the method further comprises adding an additive to at least one of the expanded woven retention device and bone hole, wherein the additive is a different material than the woven retention device. In another aspect of the invention, the additive is a slurry that is configured to form a composite material mantle that interfaces with the self-tapping screw. In another aspect of the invention, the slurry is a calcium phosphate cement. In another aspect of the invention, the material is in one of: 1) situ bone; 2) bone material and a woven retention device; and 3) bone material, a woven retention device and a slurry.

BRIEF DESCRIPTION OF THE DRAWINGS

FIG. 3A shows a side view of an embodiment of the invention.

FIG. 3B shows a close-up side view of a distal end of an embodiment of the invention.

FIG. 3C shows a close-up side view of a distal end of an embodiment of the invention.

FIG. 3D shows a close-up side view of a distal end of an embodiment of the invention.

FIG. 3E shows a close-up side view of a central portion of an embodiment of the invention.

FIG. 14A shows a side view of another embodiment of the invention.

FIG. 14B shows a close-up view of the bone hole in an embodiment of the invention.

FIG. 15A shows a perspective view of the relaxed state of another embodiment of the invention.

FIG. 15B shows a perspective view of the activated state of an embodiment of the invention.

DETAILED DESCRIPTION OF THE INVENTION

Figure 1A:
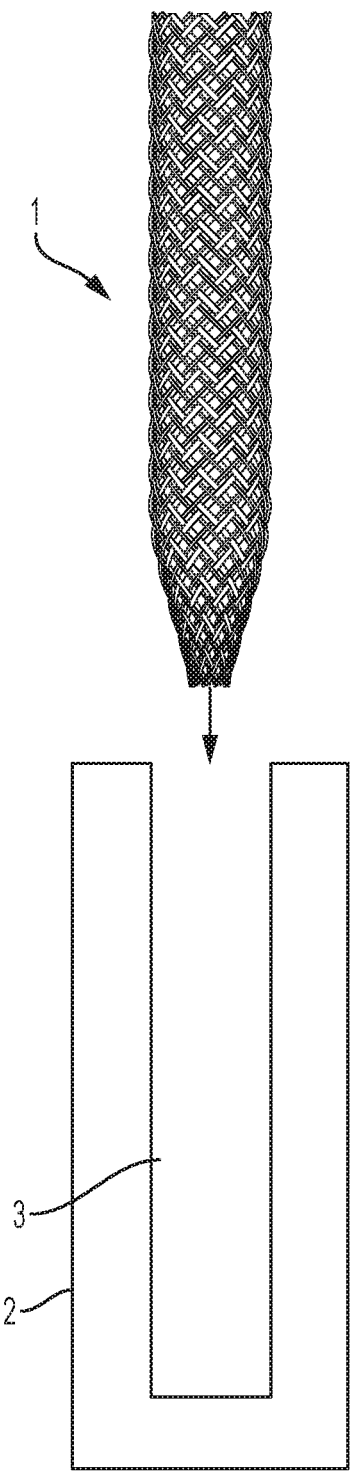
FIG. 1A shows a side view of a woven retention device in relation to a bone hole.

As shown in FIG. 1A, a woven retention device 1 may be placed in a bone hole 3 located within a bone 2. The bone hole 3 may be substantially cylindrical. The woven retention device 1 may initially be in a compressed state, as shown in FIG. 1A. The woven retention device 1 may distribute pressure from the bone screw to multiple points of contact on the exterior surface of the woven retention device 1. The woven retention device 1 may be the woven retention device disclosed in U.S. Pat. No. 8,992,537, which is incorporated by reference herein.

Figure 1B:
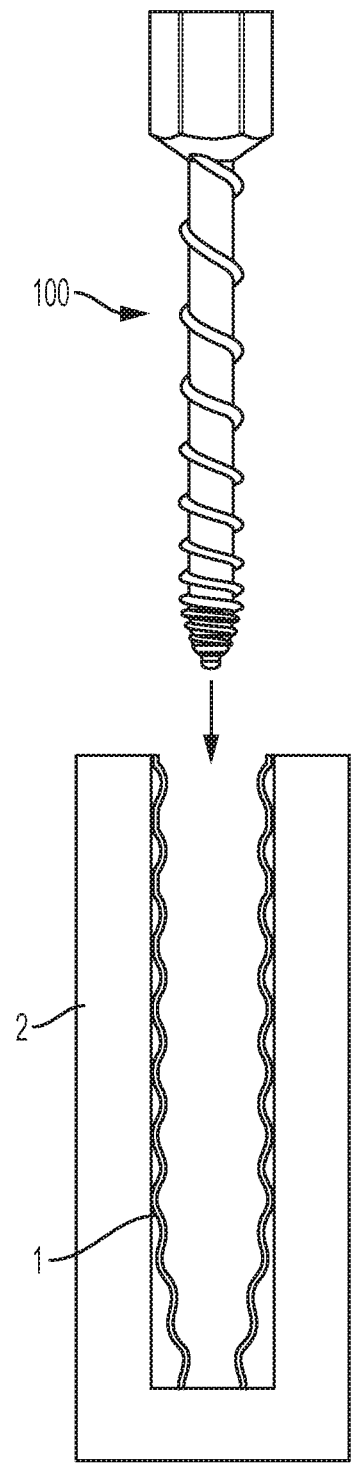
FIG. 1B shows a side view of a woven retention device placed in a bone hole.

As shown in FIG. 1B, a soft tapping device 100 having soft edges can be designed to run inside the woven retention device 1 after the compressed woven retention device has been placed in the pilot hole. The soft tapping device 100 is a substantially cylindrical insert and can expand the woven retention device 1, as shown in FIG. 1B, and then exit the bone hole 3 so that a self-tapping screw can then enter the expanded woven retention device 1 without damage to the woven retention device 1 because of the soft edges. This allows for the woven retention device 1 to be properly placed within the bone hole 3 in a desired location, with desired dilation. In an embodiment, the soft tapping device 100 may also be designed to be inserted in the bone hole before a woven retention device has been placed in the hole.

Figure 2A:
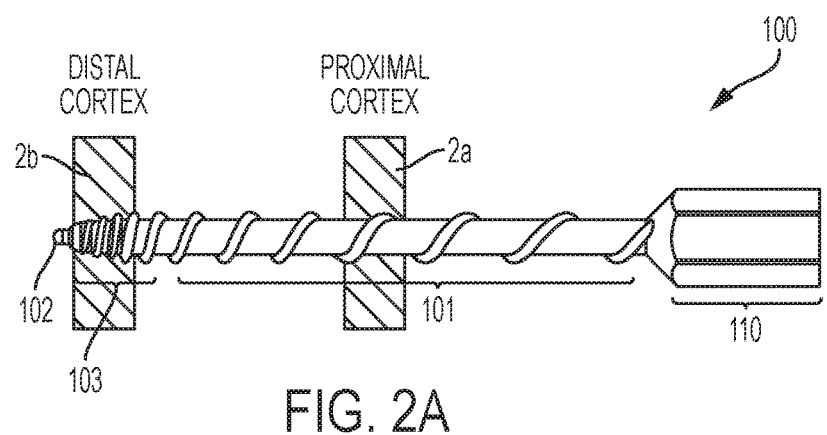
FIG. 2A shows a side view of one embodiment of the invention placed in a long bone, illustrating features that mate with the promixal and distal cortex of the bone.
Figure 2B:
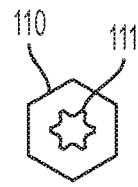
FIG. 2B shows a top view of one embodiment of the invention.

As shown in FIG. 2A, the soft tapping device 100 may be inserted into the bone hole 3, such that it passes through the proximal cortex 2a of the bone, and is inserted into the distal cortex 2b of the bone. As shown in FIG. 2B, the soft tapping device 100 includes a head 110, which includes a tool attachment surface 111 that allows for a driving tool to drive the soft tapping device 100 into the bone 2. In an embodiment, the tool attachment surface 111 may be a hex head, for example a Torx hex head. The proximal end of the shaft 101 near the head 110 is not threaded to avoid engagement with the bone and thus reduce friction and back-out resistance. The soft tapping device 100 includes a shaft portion 101, distal end 102, and a distal tip portion 103. The soft tapping device 100 further includes a thread 120 on an outer surface of the soft tapping device 100. The thread 120 may have a radially spiral configuration.

Figure 2C:
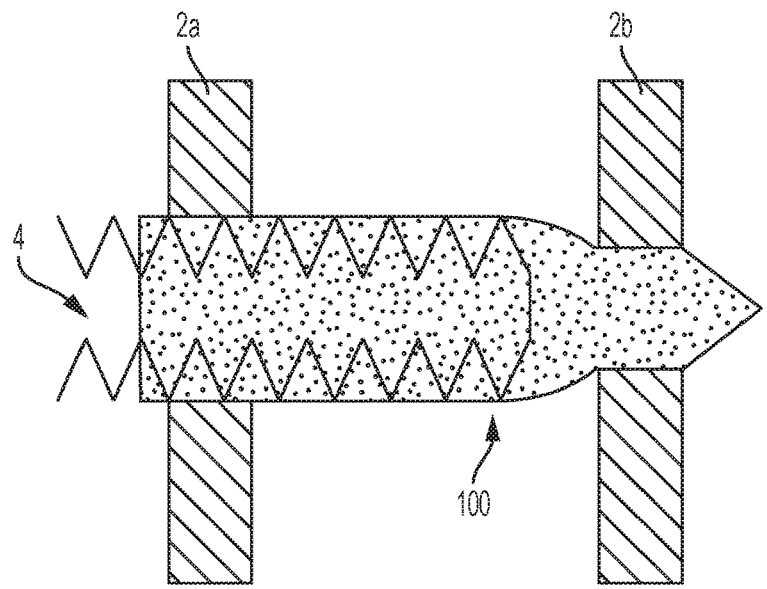
FIG. 2C shows a side view of a bone screw placed within a woven retention device placed in a bone hole.

As shown in FIG. 2C, after the soft tapping device 100 is removed from the bone 2 and/or the woven retention device 1, the woven retention device 1 is properly placed within the proximal cortex 2a and distal cortex 2b of the bone 2, and dilated to a particular diameter to accommodate a particular bone screw 4. It is understood that the soft tapping device 100 is shaped to dilate and place the woven retention device 1 without damaging the woven retention device 1.

Figure 13A:
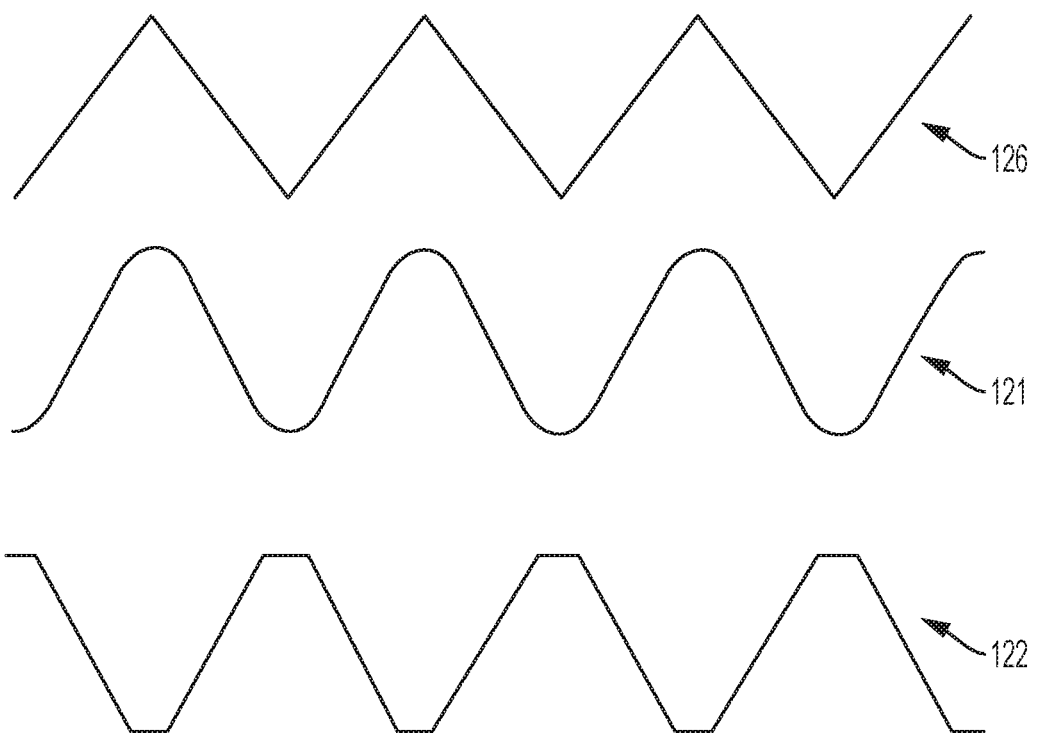
FIG. 13A shows a schematic of the threading in an embodiment of the invention.
Figure 13B:
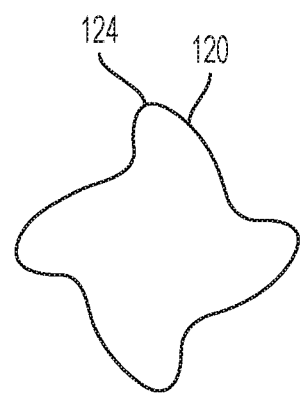
FIG. 13B shows a cross-section of the shaft in an embodiment of the invention.

The thread 120 may be of the type that compresses the bone 2, woven retention device 1, and/or composition in a bone hole 3 as described herein. For example, the thread 120 can make up the soft edges of the soft tapping device, as detailed above. In an embodiment, the soft tapping device 200 does not cut into the bone 2, woven retention device 1 and/or composition. The term "cut" is intended to be used broadly to include the separation of at least a portion of a physical object, into two or more portions, through the application of an acutely directed force. The soft tapping device 100 does not have a cutting thread like a traditional screw or tap. The soft tapping device 100 can have a non-cutting thread provided on the soft tapping device. The application of a tap (as defined broadly as a helical threaded feature) permits a localized dilating of the bone to reduce the radial force needed to compact the bone. As shown in FIG. 2A, the soft tapping device can have a helical thread at the distal portion of the device. The term "non-cutting thread" is intended to be used broadly to include threads that are of the type that preferably do not cut the bone and/or woven device, and that can be non-cutting at the crest of the thread, for example, they can be rounded at the crest of the thread, so as to not cut what it comes into contact with, for example, so as to not cut the bone and/or woven retention device. Non-cutting threads can include threads with no cutting flutes or features such as a longitudinal scallop that is intended to engage bone on its sharp edge to bite into bone. As shown in FIG. 13A, non-cutting thread can also include threads that have blunt, truncated or soft edges at the crest of the thread, whereas cutting threads 126 have triangular or sharp edges at the crest of the thread. These non-cutting threads can include rounded threads 121 and square threads 122 that do not have a sharp peak that can cut into bone. The threads of the soft tapping device can also mimic the thread geometry of the screw that is intended to be inserted into the woven retention device, so the screw follows the thread path created by the soft tapping device. In this way, the bone is dilated in a pattern that is in the shape of the screw pitch. FIG. 13B shows a cross-section of the soft tapping device 100, where threads 120 extend from the core surface of the shaft 101 and have soft edges at the radially outward-most peak or crest 124 of the thread 120.

As shown in FIGS. 3A-C, in a first embodiment, a soft tapping device 200 can be configured, as discussed above, with a shaft portion 101, distal end 102, distal tip portion 103, and thread 120. The edges of the soft tapping device 200 can be in the shape of a center bulging ridged insert where the soft tapping device gradually increases in diameter. In this embodiment, the distal tip 103 includes thread 120 wherein the thread pitch is tight enough to grab the surface, but the thread is somewhat rounded to avoid aggressive cutting. In an embodiment, a soft tapping device 200 with a 2.5 mm shaft diameter may include thread 120 that may have a 1 mm pitch at the distal tip, which increases to an 8 mm pitch at the proximal end of the distal tip. The thread may have a maximum outer diameter of 3.5 mm, and the distal tip may have a 12° taper angle. Further, the thread 120 on the shaft 101 may be coarser with a greater pitch, where the thread pitch may also increase in the proximal direction, and a thread geometry that is even rounder than at the distal tip 103. For example, as shown in FIG. 3D, the thread 120 may be rounded beginning with a radius of 0.2 mm, and height of 0.5 mm at the distal tip 103 and have a 60° thread angle. Contrastingly, as shown in FIG. 3E, the thread 120 at the shaft 101 may be more rounded with a radius of 0.32 mm, and a height of 0.55 mm, and have a 29° thread angle. The thread 120 may have a base 125 and a radially outward-most peak or crest 124. In this embodiment, the distal end 102 may be rounded with a near cortex chamfer leading edge 104 that meets the distal tip 103. This shape of the distal end 102 allows for the soft tapping device 200 to press against the bone 2 without cutting it before the first thread engages.

The soft edges of the soft tapping device 100 can expand the woven retention device and provide a "lead in" at the diameter mismatch areas. Thus, the soft edges of the soft tapping device 100, i.e. the thread 120, can act as a lead in edge that expands the woven retention device. Alternatively, or additionally, soft edges can expand, dilate and/or compress the bone material in the bone hole and provide a "lead in" at the diameter mismatch areas. As shown in FIG. 2A, the distal cortex 2b is compounded by the fact that the woven retention device 1 upon reaching the distal cortex 2b is now constrained.

Figure 4A:
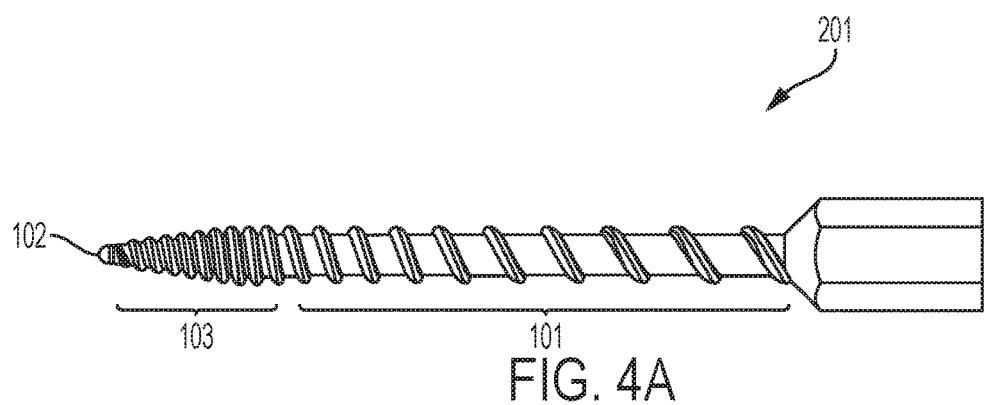
FIG. 4A shows a side view of another embodiment of the invention.
Figure 4B:
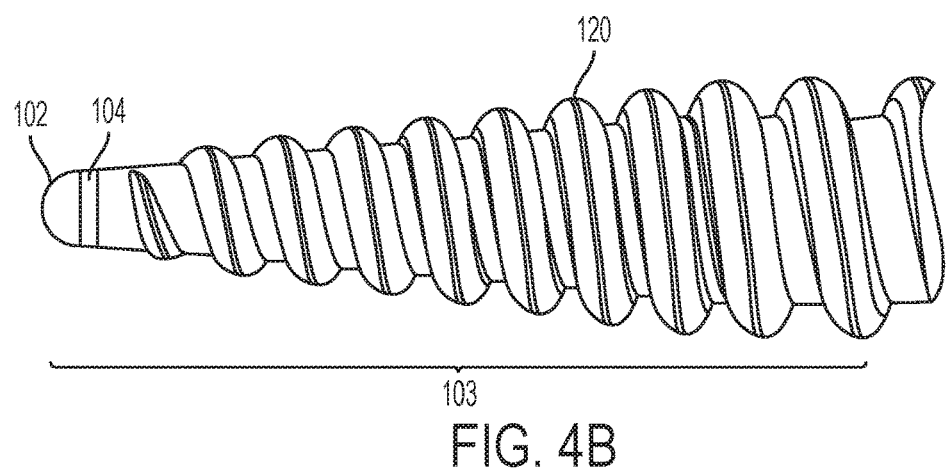
FIG. 4B shows a close-up side view of a distal end of an embodiment of the invention.
Figure 4C:
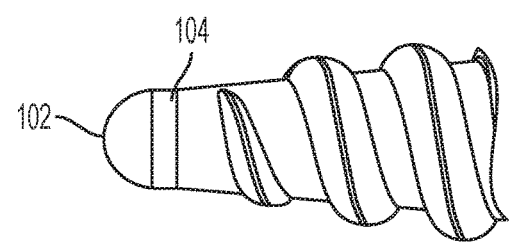
FIG. 4C shows a close-up side view of a distal end of an embodiment of the invention.

As shown in FIGS. 4A-C, in an embodiment, the distal tip 103 of a soft tapping device 201 may be tapered directly into the distal end 102, and have a greater taper than the soft tapping device 200 of FIG. 3A. In an embodiment, the thread 120 on the soft tapping device 201 may have the same shape and size on the distal tip 103 and the shaft 101. In an embodiment, the thread 120 on the shaft 101 may have an increasing pitch in the proximal direction. The thread 120 may have a finer pitch at distal tip 103 than the soft tapping device 200 of FIG. 3A. This promotes engagement with the bone 2. In an embodiment, the distal end 102 may have a narrower end that also includes a chamfer 104 between the distal end 102 and the distal tip 103. This rounded shape of the distal end 102 allows for the soft tapping device 201 to slightly pierce bone 2 and allow a smaller diameter thread to engage with the bone before tapering to a larger diameter.

While in some embodiments the soft tapping devices disclosed can be used to prepare the woven retention device for a self-tapping screw to enter the woven retention device, in another embodiment the soft tapping device can be a self-tapping screw. In an embodiment, the soft tapping device 202 may be configured where the distal end 102 and distal tip 103 is not tapered but configured with threads like a cutting tap, where the threads transition to a coarser pitch for the soft tap feature mid-shaft, and there are no threads at the proximal end. As shown in FIG. 5A-D, the distal end 102 and distal tip 103 of the soft tapping device 202 may have a thread 120 that is different than the proximal end and shaft 101. The distal tip 103 has threads that may be sharper (e.g. triangle thread versus square or rounded, as discussed with respect to FIG. 13A) and a smaller pitch to engage the proximal surface of the proximal cortex on starting and the proximal end of the distal cortex surface. This allows the screw tip to self-center and the woven retention device to displace laterally and allows the screw to engage. The proximal end has even softer thread geometry, such as rounded threads and a coarser pitch as discussed above with respect to FIGS. 3A-E. Thus, the soft edges can provide enough expansion to allow a self-tapping screw to be used. As shown in detail in FIGS. 5D-E, in an embodiment the distal tip 103 of soft tapping device 202 may have cortical thread 120 that is scalloped or saw-toothed, to further engage and cut into the bone 2. This allows for the soft tap thread 120 to engage the bone 2 quickly. In an embodiment, as shown in FIG. 5D, the thread 120 has an outer diameter of 2.45 mm at the distal tip 103, and an outer diameter of 2.6 mm at the shaft 101. The distal tip 103 may be 2.8 mm long, and the distal end 102 may have a radius of 0.85 mm. As shown in FIG. 5E, the cortical thread 120 may have a height of 0.375 mm, a 35° angle at the distal face, a 3° angle at the proximal face, and a radius of 0.05 mm at the surface.

Figure 6:
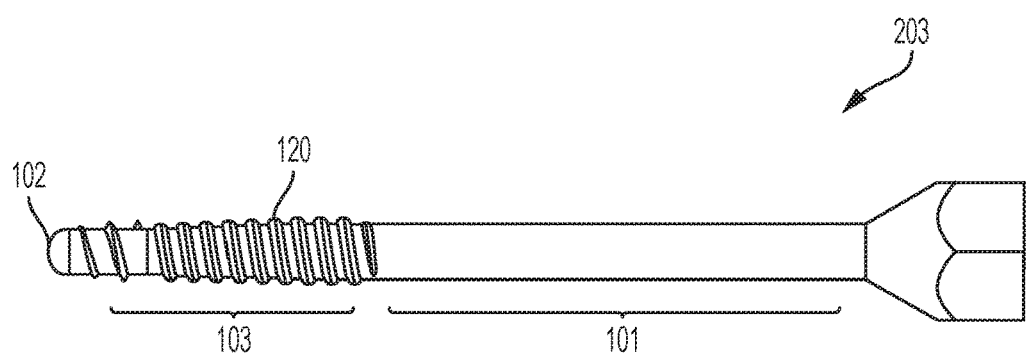
FIG. 6 shows a side view of another embodiment of the invention.

As shown in FIG. 6, in an embodiment the distal tip 103 of the soft tapping device 203 may have more rounded thread 120.

Figure 7:
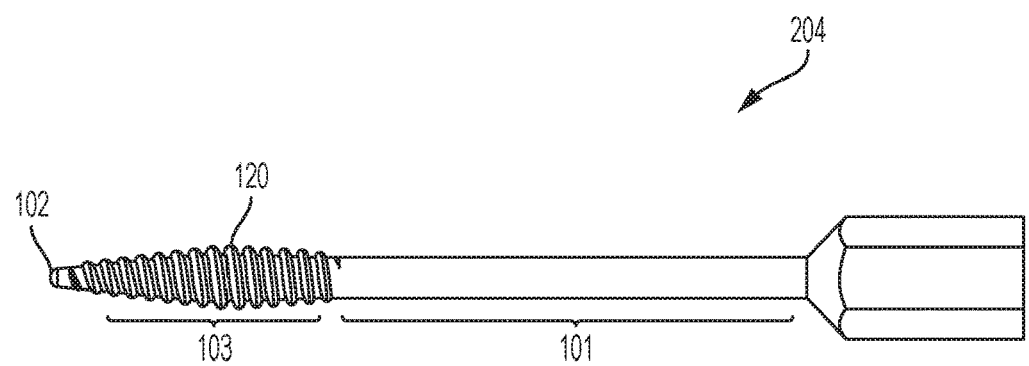
FIG. 7 shows a side view of another embodiment of the invention.

As shown in FIG. 7, in an embodiment, the soft tapping device 204 may include a distal tip 103 with a similar pitch and taper as soft tapping device 201 as shown in FIG. 4A. In an embodiment, the shaft 101 of the soft tapping device 204 is smooth, with no threading. This prevents engagement of the soft tapping device 200 with both cortices 2a, 2b at the same time.

Figure 8A:
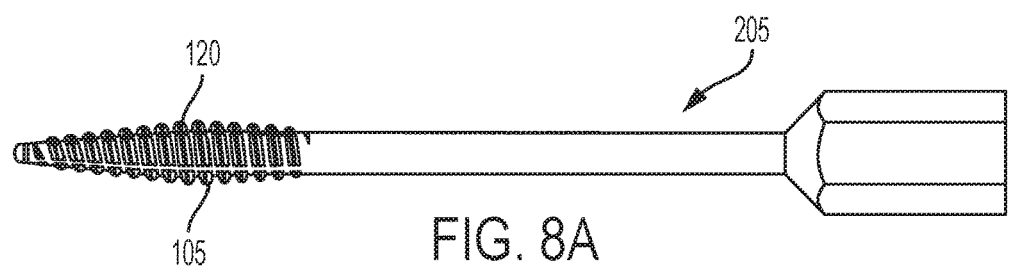
FIG. 8A shows a side view of another embodiment of the invention.
Figure 8B:
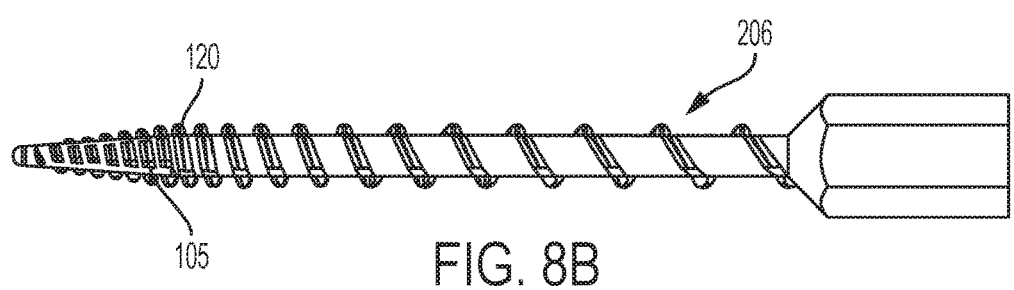
FIG. 8B shows a side view of another embodiment of the invention.

Additionally, as shown in FIGS. 8A-B, the soft tap may have longitudinal cleanout grooves 105 along part or all of the length that runs along a longitudinal axis of the soft tapping device 205, 206. This allows for the removal of debris as the soft tapping device 205, 206 moves through the bone so that any bone fragments or various other debris can exit the bone lumen. For example, FIG. 8A shows the embodiment of FIG. 7, but further including longitudinal cleanout grooves 105 along the distal tip 103 of the soft tapping device 205. Similarly, FIG. 8B shows the embodiment of FIG. 4A, but further including longitudinal cleanout grooves 105 along the distal tip 103 of the soft tapping device 206.

Figure 9A:
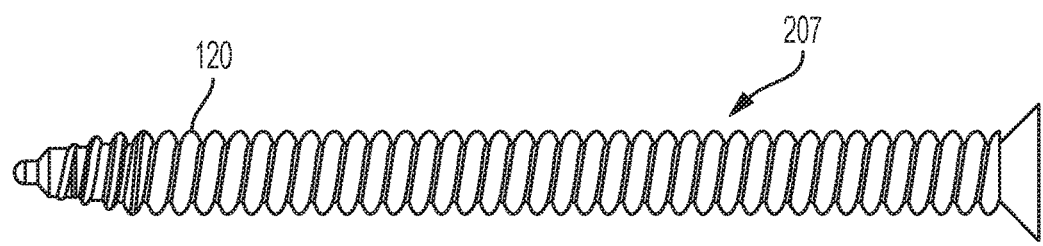
FIG. 9A shows a side view of another embodiment of the invention.
Figure 9B:
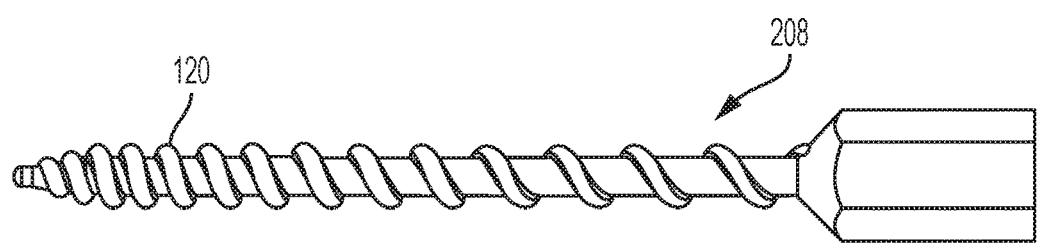
FIG. 9B shows a side view of another embodiment of the invention.
Figure 9C:
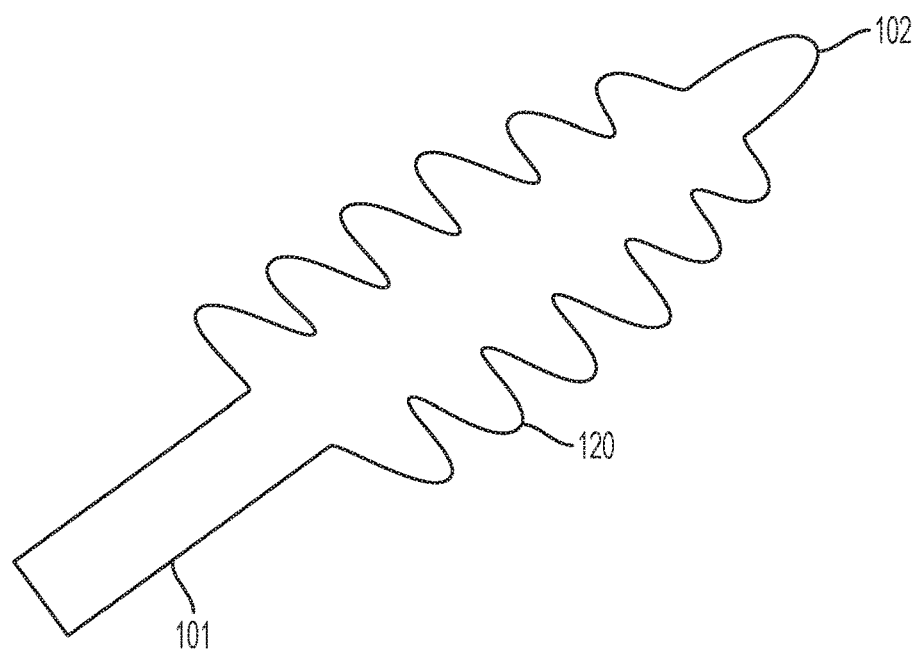
FIG. 9C shows a cross-section of another embodiment of the invention.

As shown in FIG. 9A, an embodiment of the soft tapping device 207 may have thread 120 of consistent shape and size, with an invariable very fine pitch. As shown in FIG. 9B, an embodiment of the soft tapping device 208 may have a rounded thread 120 of consistent shape and size, with a variable pitch. As shown in FIG. 9C, the soft tapping device 100 may also have a shaft 101 that tapers throughout the cylindrical body, before reaching the distal end 102. This may allow for more gentle introduction into the woven retention device 1, while providing a relatively small distal end 102.

As shown in FIGS. 10A-H, embodiments of the soft tapping devices 100 may have an increased ratio of thread height to shaft 101 core, in order to increase engagement with bone 2. In an embodiment, a shaft 101 core diameter may be 1.5 mm. In these embodiments, the soft tapping devices 100 may include a tip as shown in FIG. 5C, using a cortical thread 120 profile. In these embodiments, the taper on the tip may be very low, to allow gradual engagement of these sharper cortical threads. In these embodiments, the shaft portion 101 may have thread 120 with increased pitch with soft rounded threads, to allow for a more aggressive engagement. In an embodiment, a cortical profile thread on the tip may have a pitch of 1 mm and a tip thread outer diameter of either 2.45 or 2.5 mm. It is understood that these various embodiments may be selected by a user to fit an appropriate bone hole or pilot hole.

Figure 10A:
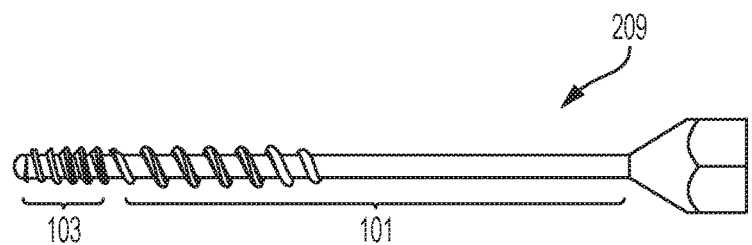
FIG. 10A shows a side view of another embodiment of the invention.
Figure 10B:
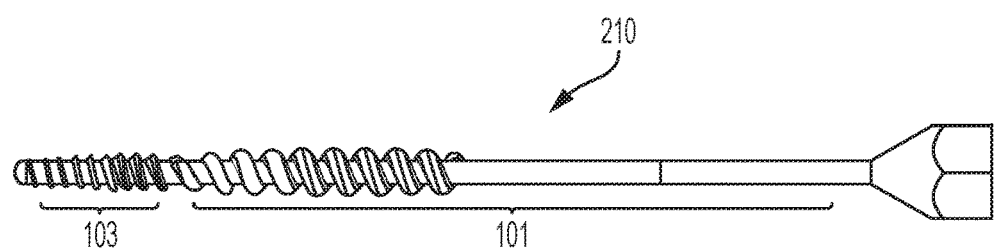
FIG. 10B shows a side view of another embodiment of the invention.
Figure 10C:
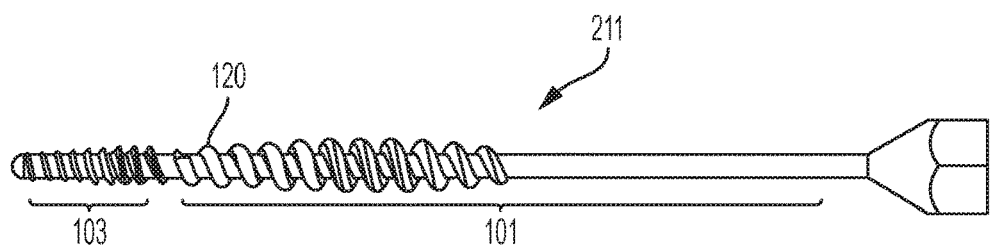
FIG. 10C shows a side view of another embodiment of the invention.
Figure 10D:
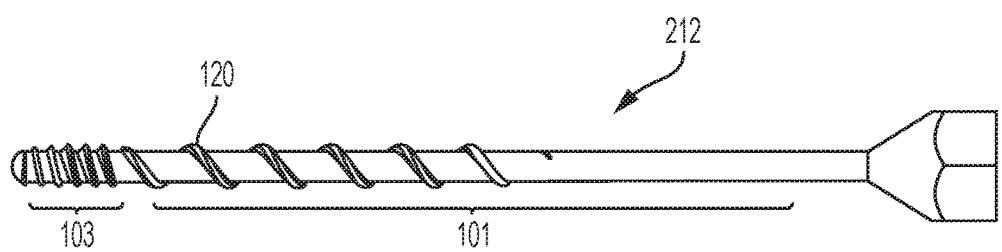
FIG. 10D shows a side view of another embodiment of the invention.
Figure 10E:
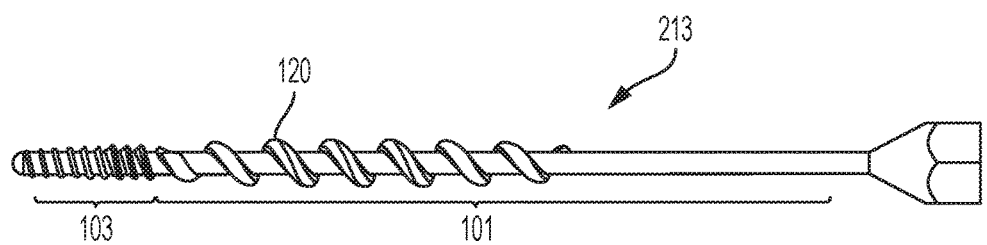
FIG. 10E shows a side view of another embodiment of the invention.
Figure 10F:
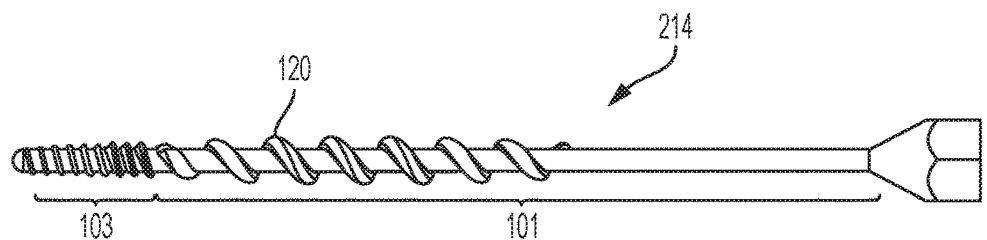
FIG. 10F shows a side view of another embodiment of the invention.
Figure 10G:
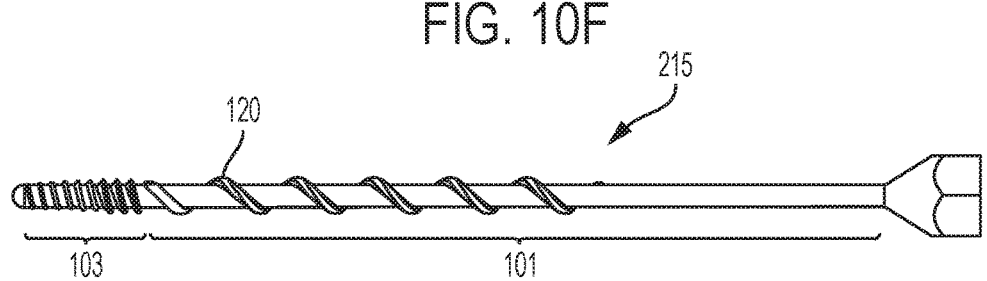
FIG. 10G shows a side view of another embodiment of the invention.
Figure 10H:
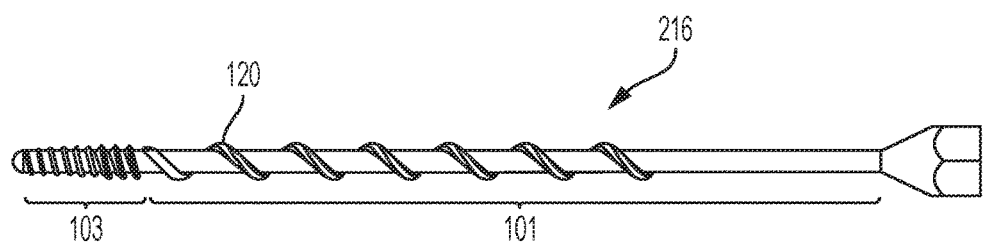
FIG. 10H shows a side view of another embodiment of the invention.
Figure 10I:
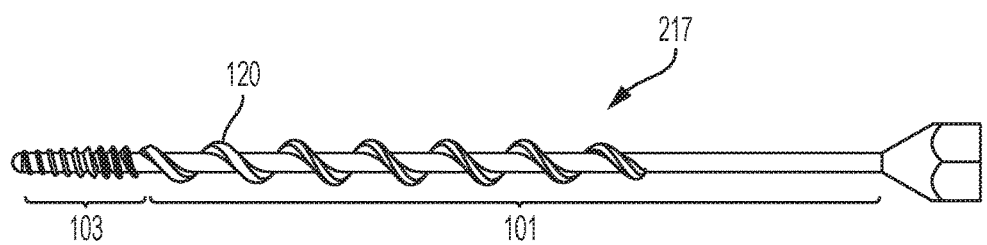
FIG. 10I shows a side view of another embodiment of the invention.

More specifically, in FIG. 10A, in an embodiment, soft tapping device 209 includes a thread pitch at the shaft portion 101 of 2 mm, with a maximum outer diameter of 2.6 mm. The soft tapping device 209 may have a 38.5 mm working length, measured from the base of the head 110 to the first thread 120. In FIG. 10B, soft tapping device 210 includes a thread pitch at the shaft portion 101 of 2 mm, with a maximum outer diameter of 3.2 mm. The soft tapping device 210 may have a 54.4 mm working length, measured from the base of the head 110 to the first thread 120. In FIG. 10C, soft tapping device 211 includes a thread pitch at the shaft portion 101 of 2 mm, with a maximum outer diameter of 3.5 mm. The soft tapping device 211 may have a 54.4 mm working length, measured from the base of the head 110 to the first thread 120. In FIG. 10D, soft tapping device 212 includes a thread pitch at the shaft portion 101 of 4 mm, with a maximum outer diameter of 2.9 mm. The soft tapping device 212 may have a 58.4 mm working length, measured from the base of the head 110 to the first thread 120. In FIG. 10E, soft tapping device 213 includes a thread pitch at the shaft portion 101 of 4 mm, with a maximum outer diameter of 3.2 mm. The soft tapping device 213 may have a 58.4 mm working length, measured from the base of the head 110 to the first thread 120. In FIG. 10F, soft tapping device 214 includes a thread pitch at the shaft portion 101 of 4 mm, with a maximum outer diameter of 3.5 mm. The soft tapping device 214 may have a 58.4 mm working length, measured from the base of the head 110 to the first thread 120. In FIG. 10G, soft tapping device 215 includes a thread pitch at the shaft portion 101 of 6 mm, with a maximum outer diameter of 2.9 mm. The soft tapping device 215 may have a 67.4 mm working length, measured from the base of the head 110 to the first thread 120. In FIG. 10H, soft tapping device 216 includes a thread pitch at the shaft portion 101 of 6 mm, with a maximum outer diameter of 3.2 mm. The soft tapping device 216 may have a 67.4 mm working length, measured from the base of the head 110 to the first thread 120. In FIG. 10I, soft tapping device 217 includes a thread pitch at the shaft portion 101 of 6 mm, with a maximum outer diameter of 3.5 mm. The soft tapping device 217 may have a 67.4 mm working length, measured from the base of the head 110 to the first thread 120.

Figure 11A:
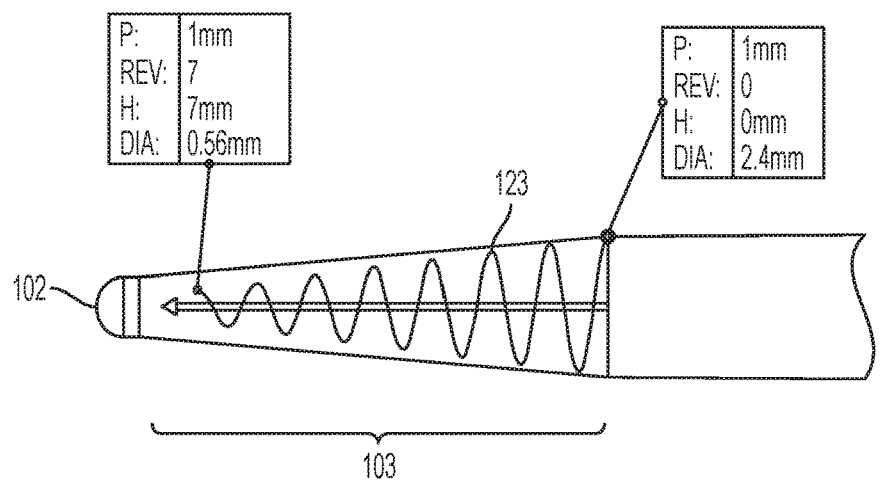
FIG. 11A shows a schematic of the threading in an embodiment of the invention.
Figure 11B:
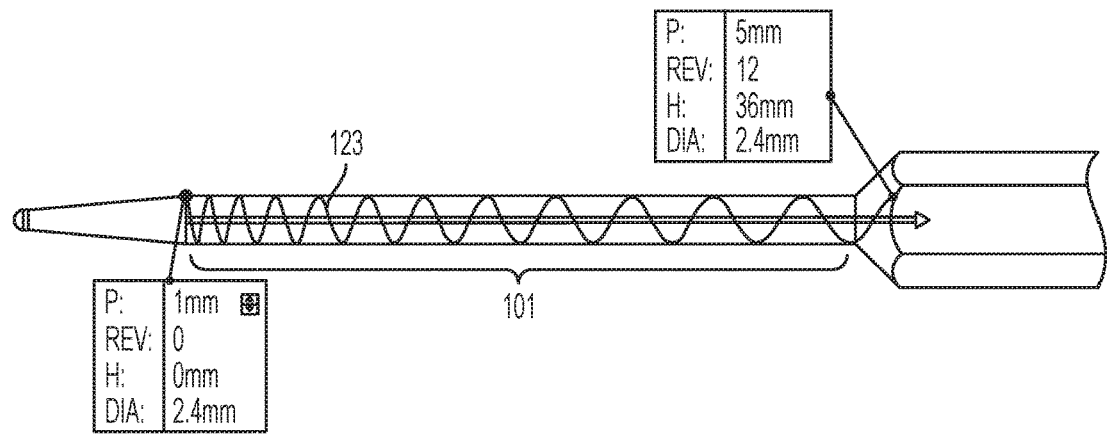
FIG. 11B shows a schematic of the threading in an embodiment of the invention.
Figure 12:
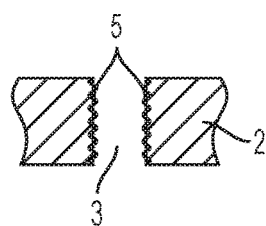
FIG. 12 shows a side view of a bone hole in an embodiment of the invention.

As shown in FIGS. 11A-B, in an embodiment the thread 120 may have a path 123 along the soft tapping device 100. As shown in FIG. 11A, at the distal tip 103, the pitch may be 1 mm, where the taper expands from 0.56 mm to 2.4 mm. The thread 120 may have 7 revolutions around the distal tip 103, with an overall length of 7 mm. As shown in FIG. 11B, at the shaft, the pitch may be 1 mm, with a consistent shaft diameter of 2.4 mm. The thread 120 may have 12 revolutions around the shaft 101, with an overall length of 36 mm. In addition, or alternatively, the soft tapping device 100 can be inserted into a bone or pilot hole 3 to compact, compress, expand and/or dilate the bone or pilot hole 3 before insertion of the woven retention device into the bone hole. This soft tapping device 100 can create a bone bed or mantle 5 in the bone material of the bone or pilot hole 3, as shown in FIG. 12, so that when the woven retention device and/or screw is introduced into the bone or pilot hole 3, the bone 2, woven retention device 1 and screw 4 engage reliably. Indeed, a self-tapping screw can be utilized with the woven retention device without damage to the woven retention device.

The soft tapping device 100 can have soft edges that create a complementary impression in the surface of the bone tissue of the bone hole 3. Thus, the complementary impression can provide recesses to the soft edges of the soft tapping device 100 that provide ridges. The soft tapping device 100 can have threads 120 that are the same or different from a screw that could create a track for screw threads to follow or not to follow. In this manner, an interface for screws to cut through for better fixation can be created.

The soft tapping device 100 can be used to push out and/or compress bone in a radial direction of the bone or pilot hole 3. Additionally, or alternatively, the soft tapping device 100 can be used to push out and/or dilate the woven retention device outward, which when the woven retention device 1 is inside the bone hole 3 can similarly push out and/or compress bone out in a direction of the bone or pilot hole 3. This pushed-out bone surface with or without the expanded woven retention device 1 inside the bone hole can be referred to as a layer or mantle, as shown in FIG. 12. The term "mantle" is intended to be interpreted broadly to encompass the bone material in the bone hole 3 that will engage and/or interface with a fastener either directly or indirectly. In one embodiment, the mantle, layer, or composite 5 can be created solely by arranging and/or configuring the existing bone material inside the bone hole 3 utilizing the soft tapping device 100. The process of soft tapping through radially expanding and/or compressing bone material radially outwardly can be repeated one or more times. The bone 2 can be prepared with the bone's own material alone before insertion of a woven retention device 1, the bone's own material and a woven retention device 1 together, e.g., after the woven retention device 1 is inserted in the bone hole 3, and/or with the bone's own material and a third element, feature or substance that can be added, e.g., added to the bone hole and/or the woven retention device. The third item can be a substance as described herein and can be different from the bone tissue and the woven retention device 1.

In an embodiment, a third substance, or an additive different from the woven retention device, can be added to the bone or pilot hole 3 before or after the woven retention device 1 has been inserted into the bone or pilot hole 3. The third substance or additive can facilitate the formation of a mantle 5 of a composite material into which a fastener can then be introduced. The third substance can be bone material, such as autograft or allograft, or bone substitute materials, such as bone cement. The third substance or additive can be a slurry. The slurry can be any of a number of slurries known in the art including calcium phosphate cement slurries. The third substance can be in situ bone, bone material and a woven retention device 1, or bone material, a woven retention device 1, and a slurry. In this manner, an insert, layer or mantle can be created from the inside of the bone or pilot hole 3. This layer or mantle 5 can provide for improved screw fixation and/or for use with various screw types including both self-tapping and non-self-tapping screws.

A bone hole 3 in accordance with the principles of the invention can be formed or created in various non-limiting ways. For example, the bone hole can be formed in a bone either by creating a pilot hole by such means as drilling, tapping, use of an awl or other instruments, or in the form of a screw stripping a pilot hole. Thus, a pilot hole as used herein can refer to a bone hole freshly drilled or stripped by a screw or formed in a bone in other ways. A soft tapping device 100 can compress and/or expand the pilot hole and provide soft edges to the pilot hole based on the exterior surface of the soft tapping device, before or after a woven retention device has been inserted into the pilot hole. A slurry can be added into the pilot hole either with the woven retention device or before insertion of the woven retention device into the pilot hole. The slurry may be a different material from the woven retention device. A fastener, such as a bone screw, can then be inserted to interface with the soft-tap created mantle 5 inside the pilot hole.

The above embodiments envision the woven retention device 1 being inserted into the bone hole 3 and then the soft tapping device 100 is inserted inside the woven retention device 1 to further dilate the hole as well as embed the woven device into the bone, forming a bone-woven device-composite mantel. However, the soft tapping device 100 can be inserted into the bone hole 3 before the woven retention device 1, thus preparing and conditioning the hole. Then the woven device is inserted. This sequence reduces insertion force for the woven device, as well as ensuring the woven device is uniformly radially expanded in the hole. All of the soft tap embodiments disclosed above can be applied in this sequence. In addition, the alternative combination of insertion the soft tapping device, then inserting the woven retention device and then re-inserting the soft tapping device into the woven retention device may provide additional benefit, depending on the condition of the bone, the bone hole size and shape, etc.

Preparing the bone hole for the woven retention device as described above can be accomplished with other configurations of the soft tapping device. The soft tapping device geometry can target a specific location within the bone hole. For example, in FIG. 14A, the soft tapping device can have features that condition the proximal end of the distal cortex only. Shown in the FIG. 14A is a spring-loaded surface 130 that deburrs and/or chamfers the proximal side of the distal cortex bone surface creating a lead-in feature. As shown in FIG. 14B, the spring-loaded deburring tool may create a chamfered hole 6 at the surface of the bone 2, which can create a larger area for the woven retention device 1 or a bone fastener to enter the bone hole 3. This feature can be incorporated with any of the above embodiments of the soft tapping device 100.

Figure 5A:
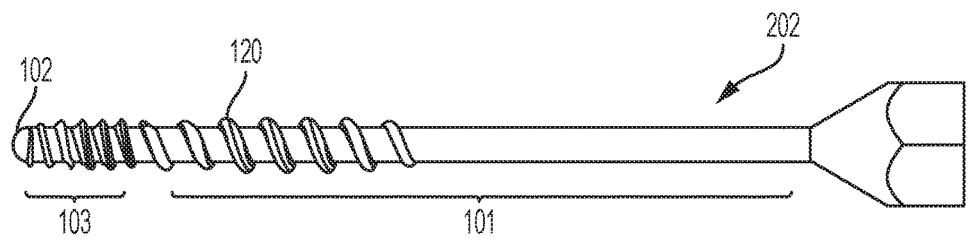
FIG. 5A shows a side view of another embodiment of the invention.
Figure 5B:
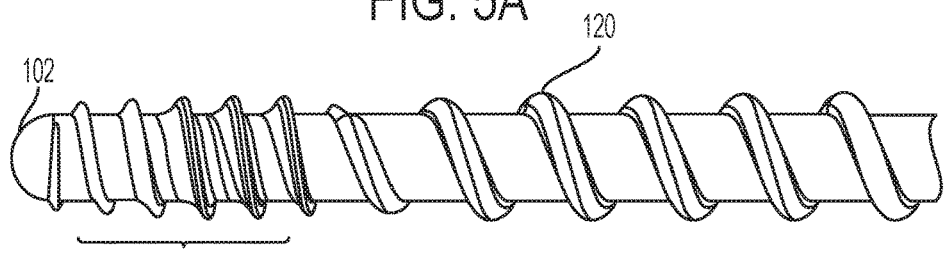
FIG. 5B shows a close-up side view of a distal end of an embodiment of the invention.
Figure 5C:
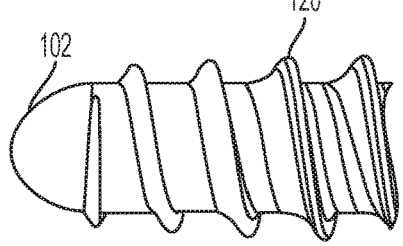
FIG. 5C shows a close-up side view of a distal end of an embodiment of the invention.
Figure 5D:
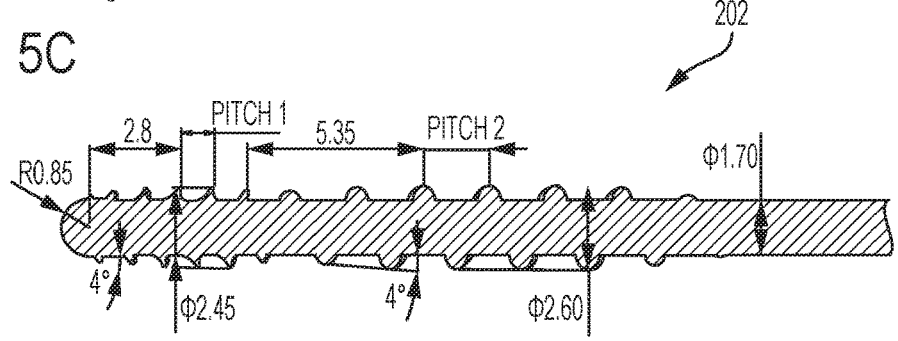
FIG. 5D shows a cross-section view of an embodiment of the invention.
Figure 5E:
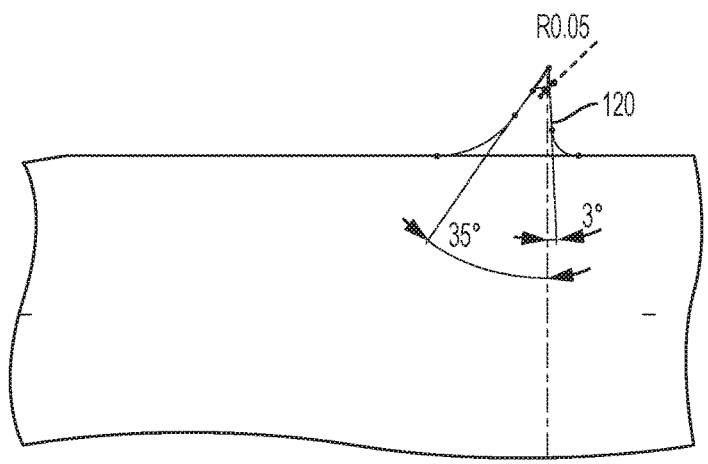
FIG. 5E shows a close-up side view of a distal end of an embodiment of the invention.

Similar to the deburring function described above, in the scenario of inserting the soft tapping device prior to insertion of the woven retention device, the soft tapping device can have more aggressive cutting features or an even separate "hard tap" device can be inserted into the bone hole to core or cut some or all of the bone hole edges to prepare the hole for the woven retention device, as discussed with respect to FIGS. 5A-B, above. This is counterintuitive to the surgeon who works to not remove bone assuming that even a small amount of bone will improve screw retention.

As shown in FIGS. 15A-B and 16A-C, embedding the woven retention device and/or compacting the bone hole surface can be accomplished with other expandable configurations. For example, a soft tapping device 301, 302 may be formed such that the relaxed tap may be inserted into the hole, and activated by compressing the proximal end of the soft tapping device 301, 302. Activating the soft tapping device increases its diameter in total or in a localized way. For example, as shown in FIGS. 15A-B, the "threads" as described above can be protrusions 310 that are expanded radially from the shaft of the soft tapping device, such as a balloon-type device that forms balloon members. FIG. 15A shows a relaxed soft tapping device 301, which is tensioned or deflated such that the shaft surface is smooth and of a uniform diameter. FIG. 15B shows an activated soft tapping device 301, where the soft tapping device 301 is either compressed in a longitudinal direction or inflated, such that the protrusions 310 expand in an outward direction from the shaft of the soft tapping device 301. In this case, the expanded feature is not intended to remove bone but to push/compact bone away from the shaft radially.

Figure 16A:
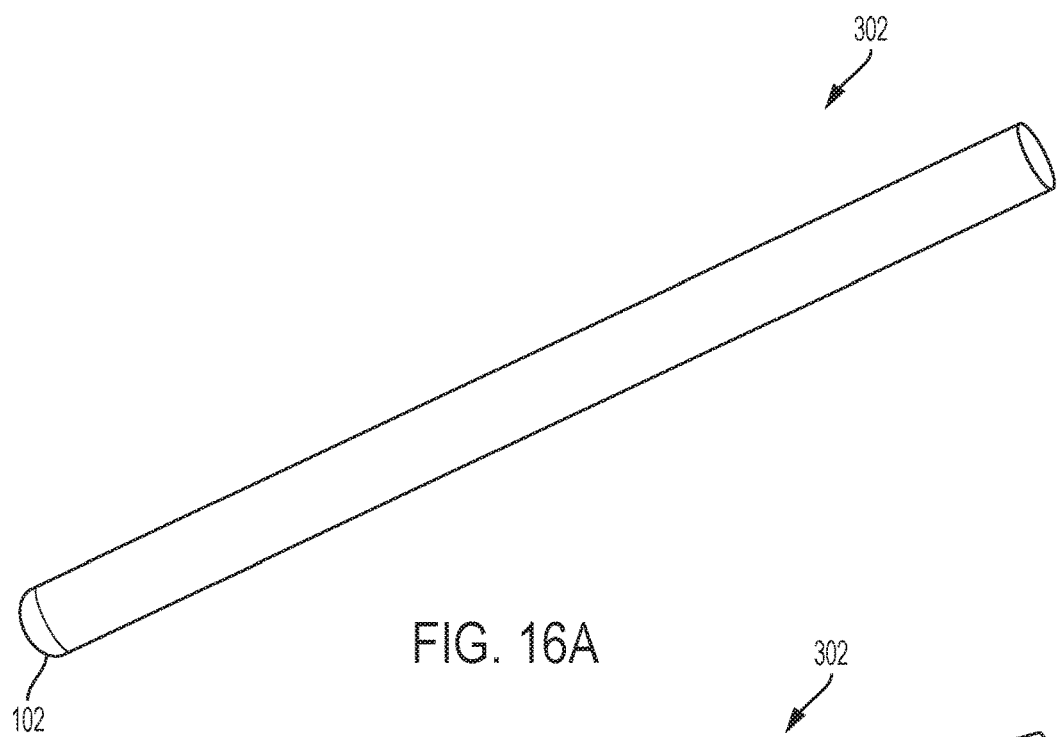
FIG. 16A shows a perspective view of the relaxed state of another embodiment of the invention.
Figure 16B:
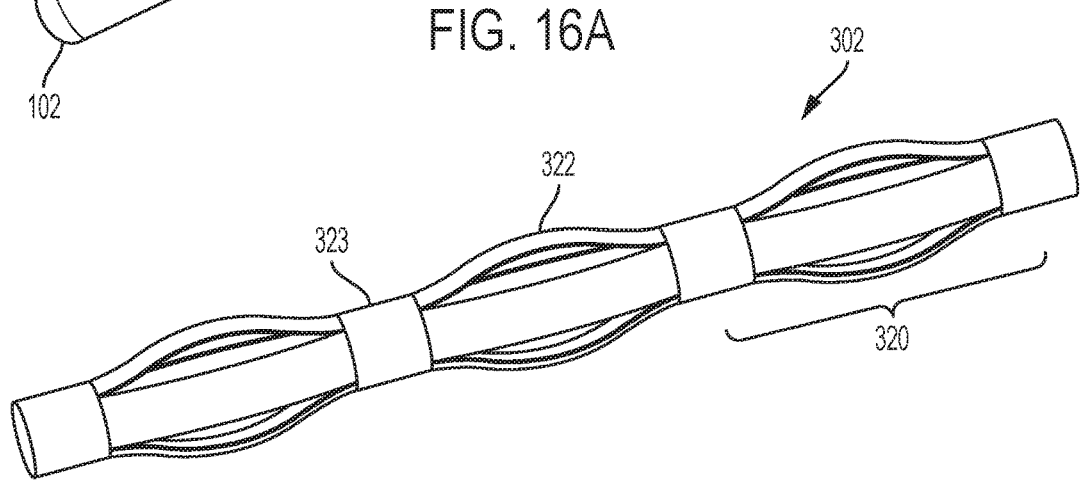
FIG. 16B shows a perspective view of the activated state of an embodiment of the invention.
Figure 16C:
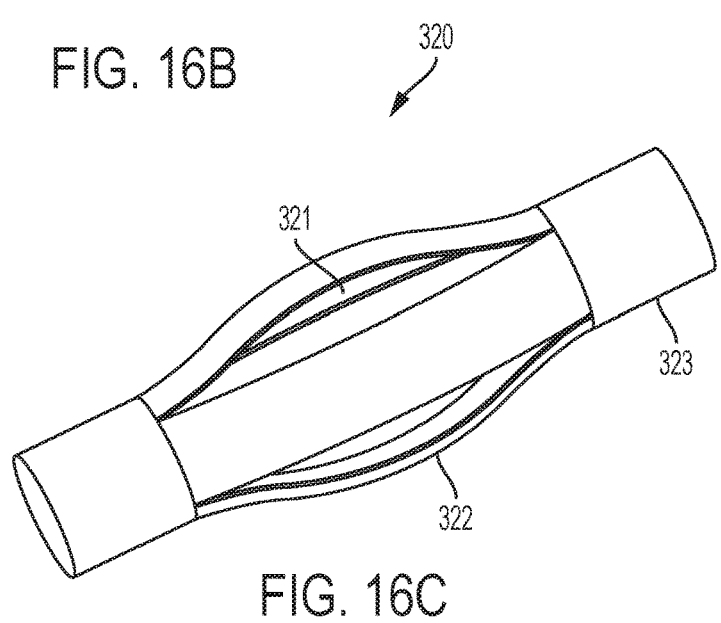
FIG. 16C shows a close-up perspective view of the activated state of an embodiment of the invention.

Alternatively, other mechanical means can be employed to expand these bone compacting features. For example, there can be singular or multiple expandable features of FIG. 16A-C that are located at various positions along the longitudinal axis, creating radially expanded features along the length. For example, FIG. 16A shows a relaxed soft tapping device 302, which is tensioned such that the shaft surface is smooth and of a uniform diameter. FIG. 16B shows an activated soft tapping device 302, where the soft tapping device 302 is compressed in a longitudinal direction, such that the protrusions 320 expand in an outward direction from the shaft of the soft tapping device 301 to create expanded portions. FIG. 16C shows the activated soft tapping device 302 in more detail, where the surface of the soft tapping device 301 includes slots 321, that form tensioned protrusion slats 322 that can expand in an outward direction from the shaft of soft tapping device 302 to create expanded portions. In this case, the expanded feature is not intended to remove bone but to push/compact bone away from the shaft radially. Other mechanical means besides the two-end constrained leaf spring-like mechanism as shown in FIGS. 15A-B and 16A-C can be used to expand a portion or multiple of portions of the device.

The various embodiments and inventions contemplated here are preferably utilized in with a woven device, for example, a woven retention device. An exemplary woven retention device contemplated for use in accordance with the principles of the invention are described and shown in, for example, U.S. Pat. No. 8,956,394, filed Aug. 5, 2014 and U.S. Pat. No. 8,992,537, filed Sep. 16, 2014, the contents of which are hereby incorporated by reference herein in their entireties.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A soft tapping device, comprising:
   a substantially cylindrical insert comprising a shaft having a proximal portion and a distal portion and sized to enter into a compressed woven retention device, the substantially cylindrical insert having protrusions that are adaptable to expand portions of the compressed woven retention device inside a pilot hole, the substantially cylindrical insert being configured to exit from the compressed woven retention device without changing the expanded portions of the compressed woven retention device, wherein the protrusions comprise a non-cutting thread and wherein the distal portion is configured with the non-cutting thread and a rounded end.

2. The soft tapping device of claim 1, wherein the non-cutting thread have a gradually increasing pitch in a proximal direction along the substantially cylindrical insert.

3. The soft tapping device of claim 1, wherein the protrusions are expanding balloon members that expand in an outward direction when the substantially cylindrical insert is compressed in a longitudinal direction.

4. The soft tapping device of claim 1, wherein the substantially cylindrical insert includes slots which form tensioned protrusion slats, wherein the protrusions are the tensioned protrusion slats; and the protrusions expand in an outward direction when the substantially cylindrical insert is compressed in a longitudinal direction.

5. The soft tapping device of claim 1, wherein the expanded portions of the compressed woven retention device allow for a self-tapping screw to insert into the woven retention device without damaging the woven retention device.

6. The soft tapping device of claim 1, wherein distal portion is configured with a first thread portion and the proximal portion is configured with a second thread portion with a coarser pitch than first thread portion of the distal portion, and wherein the second thread portion is rounder than the first thread portion.

7. A soft tapping device, comprising:
a substantially cylindrical insert configured and sized to expand portions of a substantially cylindrical hole, the substantially cylindrical insert being configured to exit from the hole without changing the expanded portions of the hole, wherein the substantially cylindrical insert comprises a shaft with a proximal portion and a distal portion, wherein the distal portion is configured with a non-cutting thread and a rounded end.

8. The soft tapping device of claim 7, wherein the non-cutting thread has a radially spiral configuration.

9. The soft tapping device of claim 7, wherein the non-cutting thread has a base and a radially outward-most peak in between the proximal portion and a distal end of the distal portion.

10. The soft tapping device of claim 7, wherein the hole is a bone hole.

11. The soft tapping device of claim 7, wherein the hole is a woven retention device configured to be disposed in a bone hole.

12. The soft tapping device of claim 7, wherein the hole is a combination of a bone hole and a woven retention device in the bone hole.

13. The soft tapping device of claim 7, further comprising a spring-loaded deburring tool on a shaft of the soft tapping device.

14. A method of creating a mantle in a bone, comprising:
inserting a compressed woven retention device into a pilot hole of a bone;
inserting a soft tapping device into the compressed woven retention device, wherein the soft tapping device has ridges that, when inserted into the compressed woven retention device, expand the woven retention device with lead in edges;
removing the soft tapping device without cutting the expanded woven retention device; and
inserting a self-tapping screw into the expanded woven retention device; wherein the ridges comprise a non-cutting thread, and a distal portion of the soft tapping device is configured with the non-cutting thread and a rounded end.

15. The method of claim 14, further comprising the step of:
expanding the compressed woven retention device with a leading edge of a ridge on the soft tapping device.

16. The method of claim 14, further comprising the step of: inserting one of a screw and a self-tapping screw into the pilot hole after the soft tapping device is removed.

17. The method of claim 16, further comprising the step of: inputting a slurry into the pilot hole before inserting the screw.

18. A method of creating a mantle for fixation in a bone hole, comprising:
providing a soft tapping device configured to compress material in a bone hole;
utilizing a soft tapping device to compress the material in the bone hole; and
inserting a woven retention device into the compressed bone hole; wherein a distal portion of the soft tapping device is configured with a non-cutting thread and a rounded end.

19. The method of claim 18, wherein the soft tapping device is configured to provide a surface of the bone hole with soft edges.

20. The method of claim 19, the compressed woven retention device being adapted to expand to fill the soft edges of the bone hole.

21. The method of claim 20, further comprising inserting a screw into the expanded woven retention device.

22. The method of claim 21, wherein the inserting the screw comprises inserting a self-tapping screw into the compressed woven retention device.

23. The method of claim 22, further comprising:
adding an additive to at least one of the expanded woven retention device and bone hole, wherein the additive is a different material than the woven retention device.

24. The method of claim 23, wherein the additive is a slurry that is configured to form a composite material mantle that interfaces with the self-tapping screw.

25. The method of claim 24, wherein the slurry is a calcium phosphate cement.

26. The method of claim 25, wherein the material is in one of: 1) situ bone; 2) bone material and a woven retention device; and 3) bone material, a woven retention device and a slurry.

* * * * *